(12) United States Patent
Rinkel et al.

(10) Patent No.: US 9,311,277 B2
(45) Date of Patent: Apr. 12, 2016

(54) METHOD OF IDENTIFYING MATERIALS FROM MULTI-ENERGY X-RAYS

(75) Inventors: Jean Rinkel, Fontaine (FR); Guillaume Beldjoudi, Grigny (FR); Jean-Marc Dinten, Lyons (FR); Georges Gonon, Claix (FR); Veronique Rebuffel, Corenc (FR)

(73) Assignee: Commissariat à l' énergie atomique et aux énergies alternatives, Paris (FR)

( * ) Notice: Subject to any disclaimer, the term of this patent is extended or adjusted under 35 U.S.C. 154(b) by 583 days.

(21) Appl. No.: 13/807,828

(22) PCT Filed: Jun. 28, 2011

(86) PCT No.: PCT/EP2011/060818
§ 371 (c)(1),
(2), (4) Date: Dec. 31, 2012

(87) PCT Pub. No.: WO2012/000993
PCT Pub. Date: Jan. 5, 2012

(65) Prior Publication Data
US 2013/0110438 A1     May 2, 2013

(30) Foreign Application Priority Data

Jun. 29, 2010 (FR) .................................... 10 55230

(51) Int. Cl.
*G06F 17/18* (2006.01)
*G01T 7/00* (2006.01)
(Continued)

(52) U.S. Cl.
CPC .............. *G06F 17/18* (2013.01); *G01N 23/087* (2013.01); *G01T 1/366* (2013.01); *G01T 7/005* (2013.01)

(58) Field of Classification Search
CPC ...... G01N 23/087; G01T 1/366; G01T 7/005; G06F 17/18
USPC .......... 702/85, 97, 179, 181; 378/53, 62, 98.9
See application file for complete search history.

(56) References Cited

U.S. PATENT DOCUMENTS

| 4,029,963 A | 6/1977 | Alvarez et al. |
| 5,206,174 A | 4/1993 | Gehrke et al. |

(Continued)

FOREIGN PATENT DOCUMENTS

| EP | 1 429 158 A2 | 6/2004 |
| EP | 2 071 722 A1 | 6/2009 |

(Continued)

OTHER PUBLICATIONS

International Search Report & Written Opinion issued Aug. 12, 2011 in Application No. PCT/EP2011/060818.

(Continued)

*Primary Examiner* — John H Le
(74) *Attorney, Agent, or Firm* — Oblon, McClelland, Maier & Neustadt, L.L.P.

(57) ABSTRACT

A calibration method for a device for identifying materials using X-rays, including: a) determining at least one calibration material and, for each calibration material, at least one calibration thickness of this material, b) measuring, for each of the calibration materials and for each of the selected calibration thicknesses, attenuation or transmission coefficients for X radiation, c) calculating statistical parameters from the coefficients, d) determining or calculating, for each calibration material and for each calibration thickness, a presence probability distribution law, as a function of the statistical parameters.

23 Claims, 11 Drawing Sheets

(51) Int. Cl.
  *G01N 23/087* (2006.01)
  *G01T 1/36* (2006.01)

(56) References Cited

U.S. PATENT DOCUMENTS

| | | | |
|---|---|---|---|
| 5,524,133 | A | 6/1996 | Neale et al. |
| 5,821,538 | A | 10/1998 | De Antoni et al. |
| 5,838,758 | A * | 11/1998 | Krug et al. ............ 378/53 |
| 6,018,562 | A | 1/2000 | Willson |
| 6,069,936 | A | 5/2000 | Bjorkholm |
| 7,126,410 | B2 | 10/2006 | Rostaing et al. |
| 7,615,753 | B2 | 11/2009 | Audebert et al. |
| 7,652,242 | B2 | 1/2010 | Ouvrier-Buffet et al. |
| 8,184,769 | B2 * | 5/2012 | Fox et al. ............ 378/53 |
| 2003/0086523 | A1 | 5/2003 | Tashiro et al. |
| 2007/0286329 | A1 | 12/2007 | Wang et al. |
| 2008/0025385 | A1 | 1/2008 | Barat et al. |
| 2009/0129544 | A1 | 5/2009 | Chen et al. |
| 2009/0152448 | A1 | 6/2009 | Ouvrier-Buffet et al. |
| 2011/0098980 | A1 | 4/2011 | Ouvrier-Buffet et al. |
| 2012/0239310 | A1 | 9/2012 | Ouvrier-Buffet et al. |

FOREIGN PATENT DOCUMENTS

| | | |
|---|---|---|
| FR | 2 738 693 | 3/1997 |
| FR | 2 864 628 | 7/2005 |
| FR | 2 870 603 | 11/2005 |
| WO | WO 2008/142446 A2 | 11/2008 |
| WO | WO 2009/024818 A1 | 2/2009 |

OTHER PUBLICATIONS

Search Report issued May 20, 2011 in French Application No. 1055230 (With English Translation of Category of Cited Documents).

ANSI N42.14-1999 "American National Standard for Calibration and use of Germanium Spectrometers for the Measurement of Gamma-Ray Emission Rates of Radionuclides", ANSI N42.14-1999 (revision of ANSI N42.14-1991), 1999, American National Standards Institutes, pp. 7,13,15,86,89,134.

Lucian Wielopolski, et al., "Prediction of the Pulse-Height Spectral Distortion Caused by the Peak Pile-Up Effect", Nuclear Instruments and Methods, 133, 1976, pp. 303-309.

V. D. Ryzhikov, et al., "A spectrometric approach in radiography for detection of materials by their effective atomic number", Nuclear Intruments and Methods in Physics Research A, vol. 603, No. 3, XP 026097538, Feb. 2009, pp. 349-354.

Sergey V. Naydenov, et al., "Direct reconstruction of the effective atomic number of materials by the method of multi-energy radiography", Nuclear Intruments and Methods in Physics Research B, vol. 215, No. 3-4, XP 004486776, Feb. 2004, pp. 552-560.

L. A. Lehmann, et al., "Generalized image combinations in dual KVP digital radiography", Medical Physics, vol. 8, No. 5, XP 002631532, Sep./Oct. 1981, pp. 659-667.

Robin P. Gardner, et al., "A Generalized Method for Correcting Pulse-Height Spectra for the Peak Pile-up Effect due to Double Sum Pulses—Part I: Predicting Spectral Distortion for Arbitrary Pulse Shapes", Nuclear Instruments and Methods, vol. 140, No. 2, XP-002595352, Jan. 15, 1977, pp. 289-296.

Lucian Wielopolski, et al., "A Generalized Method for Correcting Pulse-Height Spectra for the Peak Pile-up Effect due to Double Sum Pulses—Part II: The Inverse calculation for Obtaining true from Observed Spectra", Nuclear Instruments and Methods, vol. 140, No. 2, XP-002595351, Jan. 15, 1977, pp. 297-303.

N. P. Barradas, et al., "Accurate Calculation of Pileup Effects in PIXE Spectra from first Principles", X-Ray Spectrometry, vol. 35, XP-007914254, Jan. 1, 2006, pp. 232-237.

Fred H. Tenney, "Idealized Pulse Pileup Effects on Energy Spectra", Nuclear Instruments & Methods in Physics Research, vol. 219, No. 1, XP-002595353, Jan. 1, 1984, pp. 165-172.

Sergey V. Naydenov, et al., "Multi-energy approach in radiography and introscopy", Nuclear Instruments and Methods in Physics Research A, vol. 537, 2005, pp. 462-466.

Richard D. R. MacDonald, "Design and Implementation of a Dual-Energy X-Ray Imaging System for Organic Material Detection in an Airport Security Application", Proceedings of SPIE, vol. 4301, 2001, pp. 31-41.

Thomas Trigano, "Traitement statistique du signal spectrométrique: étude du désempilement de spectre en énergie pour la spectrométrie Gamma", LTCI—Télécom ParisTech, Version 1, Jul. 11, 2006, 179 pages (with English abstract).

Combined Chinese Office Action and Search Report issued Jan. 6, 2015 in Patent Application No. 201180040433.4 (with English Translation).

U.S. Appl. No. 14/677,293, filed Apr. 2, 2015, Popa, et al.

* cited by examiner

Counting image       Identification image

METHOD OF IDENTIFYING MATERIALS FROM MULTI-ENERGY X-RAYS

TECHNICAL FIELD AND BACKGROUND OF THE INVENTION

The invention relates to the field of x-ray and gamma-ray analysis, particularly, but not only, high flow.

The applications of x- or γ-rays have developed in the field of non-destructive testing and in security applications (detection of explosive materials using multi-energy radiography, for example).

One particular industrial application of the invention is the detection of explosives to check luggage using continuous radiography. But other applications are also possible, in particular during intense X and/or gamma photon flow measurements by measuring the photon flow transmitted by the sample.

Moreover, the known techniques are very difficult to make compatible with the current requirements for luggage inspections: the method must be fast, but also precise and compatible with security. In particular, the conveyance speed of the luggage requires that the energy of the photons transmitted through the luggage be measured, generally over a short time (several ms) with an incident photon flow that may be high (several tens of Mphotons/mm$^2$/s) to keep sufficient statistics.

To that end, various types of detectors may be used, including sensors measuring an average deposited energy or, more recently, spectrometric sensors. In this type of application, the object to be tested is placed between an ionizing ray source, generally an x-ray source, and the detectors. As a result, the detectors measure the radiation transmitted by the object.

In the prior art, the latter parts are generally non-spectrometric detectors, delivering a signal depending on the intensity of the X radiation. These are for example scintillation detectors not having a spectrometric function. Such detectors are superimposed on one another, intermediate screens being able to be placed between two successive detectors. Generally, two detectors are used, under the name of "sandwich sensors": a first detector superimposed on a second detector, the first detector being placed near the object to be tested. The first detector is generally small, such that it primarily absorbs the low-energy photons. The second detector is generally larger, so that it primarily absorbs the high-energy photons. Thus, by using these first and second detectors, one respectively measures an intensity of the low-energy component and an intensity of the high-energy component of the radiation transmitted by the object. By comparing these measurements to measurements done with the same detectors, but without the object between these detectors and the source (or direct measurements), attenuation coefficients of the object are estimated, at low energy (using the first detector) and high energy (using the second detector).

The measured attenuation coefficients are then compared with the reference coefficients obtained in the same way, the object then being replaced by reference materials, with known thicknesses and natures.

Finally, this amounts to determining which of the reference materials provides reference attenuation coefficients closest to those measured with the analyzed object. It is then considered that the material of the analyzed object has the characteristics (nature, thickness) of this reference material said to be closest.

Recently, superimposed detectors have advantageously been replaced by a detector having a spectrometric function. It is then possible to obtain a transmission function of the object subjected to X radiation. From this function, it is possible to determine the attenuation coefficient parameters, in different energy ranges, which can be compared to the parameters of known materials.

Thus, irrespective of the detection technique used (superimposed non-spectrometric detectors or spectrometric detector), the problem arises of identifying a material by comparing attenuation coefficients measured on an unknown object to reference coefficients done on reference materials.

The known approaches are based on identifying the reference material having the attenuation coefficients closest to those established with an unknown object. But they are not reliable, in particular when the measurements are done quickly. The signal acquisitions being short, the related uncertainty is high. The problem also arises of finding a method for identifying a material, using x or γ rays, which is more reliable than the methods currently known.

Lastly, as already explained, one of the applications is luggage inspection, for example in an airport, for explosives detection.

Now, in this case, the problem arises of performing an inspection very quickly, so as to be able to examine luggage successively, in very short periods, compatible with the arrival of travelers' luggage in a detection device.

BRIEF DESCRIPTION OF THE INVENTION

A calibration method is firstly disclosed, for a device for identifying materials using X-rays, including:

a) determining at least one calibration material—or a plurality of calibration materials—and, for each calibration material, at least one calibration thickness—or a plurality of calibration thicknesses—of this material, b) measuring, for each of the calibration materials and for each of the chosen calibration thicknesses, N attenuation or transmission coefficients αi for X radiation, with N≥2, c) calculating statistical parameters from said coefficients, d) determining or calculating, for each calibration material and for each calibration thickness, or for each of at least part of the calibration thicknesses, a presence probability distribution law f, as a function of said statistical parameters.

In one embodiment, called discrete mode, the calibration method also includes the following step:

e) determining, for each coefficient αi, $\alpha_{i,pi}$ measurable discrete values, with 1≤pi≤Pi, Pi being the index of the maximum measurable coefficient $\alpha_{i,pi}$.

This step may also be followed by the calculation, for each N-uplet ($\alpha_{1,p1}, \alpha_{2,p2}, \ldots \alpha_{N,pN}$,), of the value of each of the probability densities established in step d), then possibly determining, for each N-uplet ($\alpha_{1,p1}, \alpha_{2,p2}, \ldots \alpha_{N,pN}$,), the nature and thickness of the material for which the probability density is maximal.

In one of the above methods, the establishment, during the calibration phase, of statistical and distribution parameters as a function of these parameters, will then allow a very rapid examination of any object, in particular a material that must be characterized, i.e. for which one wishes to identify the nature and also, potentially, the thickness.

Such a method may also have a step c') for determining interpolated statistical parameters, for thickness values, called interpolation thicknesses, other than those determined during step a). These interpolations are done from previously established statistical parameters.

Such a method can then include the following additional step d'):

d') calculating, for each calibration material and each of at least part of the interpolation thicknesses chosen for each calibration material, a presence probability distribution law, as a function of said statistical parameters.

This method may then include determining, for each attenuation or transmission coefficient αi, $\alpha_{i,pi}$ measurable discrete values, with 1≤pi≤Pi, Pi being the index of the maximum measurable coefficient $\alpha_{i,pi}$, then possibly calculating, for each N-uplet $(\alpha_{1,p1}, \alpha_{2,p2}, \ldots \alpha_{N,pN.})$, the value of each of the probability densities established in step d'). It may also include determining, for each N-uplet $(\alpha_{1,p1}, \alpha_{2,p2}, \ldots \alpha_{N,pN.})$, the nature and thickness of the material for which the probability density is maximal.

In other words, the data obtained from the interpolations will make it also possible to complete the data relative to the statistical parameters, and the presence probability distribution data. The set of data is then completed, which may be used during identification of a material.

One distribution example which may be used is a presence probability distribution of the Gaussian type.

Preferably, during step b), for at least part of the calibration thicknesses of each calibration material, at least N_stat measurements are done, with 100≤N_stat≤$10^4$. Very good statistics are thus achieved during the calibration phase, which makes it possible to ensure very good accuracy during the subsequent measurement phase.

According to one preferred embodiment, step b) comprises the calculation of at least two transmission or attenuation coefficients $(\alpha_1, \alpha_2)$, in at least two energy bands or ranges, one for low energy and one for high energy, for each of the calibration materials and for each of the selected calibration thicknesses.

Preferably, a first energy band or range is between 15 and 50 keV and a second energy band or range is between 40 and 120 keV or between 50 keV and 120 keV.

A method is further disclosed, for identifying a material using x radiography, including:
  measuring, for this material, attenuation or transmission coefficients of an x radiation,
  determining at least two transmission or attenuation coefficients $(\alpha_1, \alpha_2)$, in said at least two energy bands or ranges, from said coefficients measured for this material,
  determining at least the nature of the material, by identifying the probability distribution, among the distributions as determined above, for which the transmission or attenuation coefficients determined for this material have the greatest value.

A device is also disclosed, for identifying X radiography materials, including:
  a) means for determining a plurality of calibration materials and, for each material, a plurality of thicknesses for that material,
  b) a radiation source, a detector, and means for determining, for each of the calibration materials and each of the selected thicknesses, attenuation or transmission coefficients for an X ray,
  c) means for calculating statistical parameters from said coefficients,
  d) means for calculating a presence probability distribution, as a function of said statistical parameters,
  e) means for determining at least the nature of a material, as a function of said probability distributions.

Here again, the determination of the nature of a material may very advantageously benefit from the prior determination of a probability distribution function. Despite the high number of calculations to be performed, once the measurements are done, the determination of the material is very quick, much shorter than 1 ms.

A method or a device as disclosed may use means, for measuring the attenuation or transmission coefficients, including:
  a spectrometric detector, i.e. able to deliver an energy spectrum of the measured radiation,
  or two associated non-spectrometric detectors (of the "sandwich" sensor type), or more than two associated non-spectrometric detectors,
  or a single non-spectrometric detector, the latter part then being successively exposed to an incident radiation with different energy.

Preferably, such a device includes an X radiation source making it possible to emit an incident photon fluence flow rate at least equal to $10^6$ mm$^{-2}$s$^{-1}$.

According to one particular embodiment, such a device further includes means for determining attenuation or transmission coefficients, called interpolated coefficients, for thickness values, called interpolation thicknesses, other than those for which one or several measurements are done and, possibly, means for determining statistical parameters from said interpolated coefficients and for calculating a presence probability distribution, as a function of said statistical parameters.

Means may be provided to calculate at least two attenuation coefficients $(\alpha_1, \alpha_2)$, in at least two energy bands or ranges, one for low energy and one for high energy, from attenuation or transmission data measured for a material.

According to one embodiment, the statistical parameters of a device or a method as disclosed include at least the average and the standard deviation of each of the attenuation coefficient, and the coefficient of correlation between the calculated transmission or attenuation coefficients.

It is also possible to provide a step, and means, for discretization of the transmission or attenuation coefficients $(\alpha_1, \alpha_2)$ in N values.

DETAILED DESCRIPTION OF EMBODIMENTS OF THE INVENTION

One discloses here the identification of the nature and/or thickness of an unknown object, by placing said object between a radiation source (X or gamma) and a detector (or detector assembly). This identification assumes the measurement of the radiation transmitted by the object, this measurement being compared with a measurement of the radiation without the object being inserted between the source and the detector.

Attenuation or transmission coefficients refer to coefficients obtained from comparing the radiation measurements with and without the object between the radiation source and the detector(s). These measurements may respectively be designated as I and $I_0$. The comparison between I and $I_0$ generally comprises a ratio between I and $I_0$. In the most frequent case, and as will be the case in the continuation of the text, these coefficients are attenuation coefficients, i.e. they are determined from the attenuation function of said object.

But it may also be applied to transmission coefficients, i.e. coefficients established from the transmission function of the object.

It is recalled that if I is the intensity of the radiation transmitted by the object, and $I_0$ is the intensity of the radiation measured without the object, the function $$\frac{I}{I_0}$$

conventionally designates the transmission function, noted as TR, while the function $$-\ln\left(\frac{I}{I_0}\right)$$

conventionally designates the attenuation function, noted as ATT. In the continuation of the description, and non-limitingly, attenuation coefficients are used.

Figure 1A:
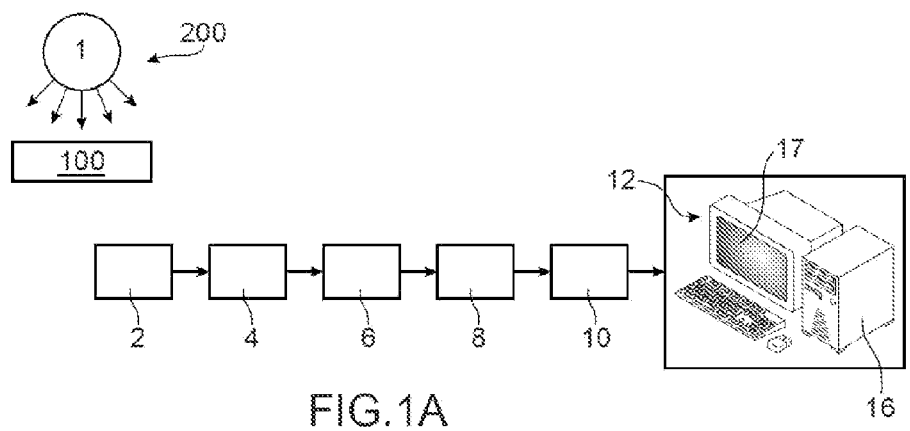
FIGS. 1A and 1B show examples of a device as disclosed.

A first exemplary embodiment of a device to which the present teaching may be applied will be provided, relative to FIG. 1A.

A preferably spectrometric sensor concerned here is preferentially a direct conversion sensor, i.e. the incident X photons on the sensor interact with a biased semiconductor material (CdTe, for example), and generate a cloud of electronic charges (typically 10,000 electrons for a 60 keV X photon).

These charges are then collected by electrodes and form a transient electrical signal called a pulse. After digitization, the impulses are classified in different channels according to their amplitude, and an energy value is assigned to each channel. The distribution by channels of each interaction corresponds to the energy spectrum of the radiation having interacted with the irradiated object, or energy spectrum of the detected radiation. The radiation is preferably X or gamma photon radiation.

A device or a spectrometry chain 1, therefore includes the following elements:

a radiation source 1, which emits a radiation 200, for example with an incident photon fluence rate between $10^6$ mm$^{-2}$s$^{-1}$ and $10^8$ mm$^{-2}$s$^{-1}$, a sensor 2, for example of the direct conversion type, also for example made from a semiconducting material such as CdTe or CdTe:Cl, or CdTe:In or CdZnTe or CdMnTe or HgI$_2$ or AsGa or Si or TlBr. This sensor is provided with two electrodes at the terminals of which a signal pulse translates an interaction of a radiation or a photon with the material of the sensor and the generation of a cloud of electronic charges (typically 1,000 electrons for an X photon of 60 keV), in the material of the sensor that results from this interaction. The charges are then captured by the two electrodes between which the required potential difference has been established. If the collection is complete, the integral of the measured pulse is proportionate to the energy deposited by the incident particle. This sensor is for example parallelepipedal, having two electrodes on two opposite faces, the electrodes being able to be oriented perpendicular to the incident radiation; in the case of a CdTe detector, the surface perpendicular to the incident radiation is for example 800 μm*800 μm, and the thickness of the detector (in the direction of average propagation of the incident radiation) is, further as an example, 3 mm.

a charge preamplifier 4, an amplifier 6, an analog/digital converter 8, means 10 for performing processing of the signal shaped and digitized by the means 4, 6, 8, and for forming a spectrum of a radiation according to a number of channels Nc (≥2), each channel i corresponding to an energy range between $E_i$ and $E_i+\Delta E_i$, $\Delta E_i$ then corresponding to the energy width of the channel i. $\Delta E_i$ may be identical for each channel, so that for any channel i, $\Delta E_i=\Delta E$, $\Delta E$ then being a constant, means 12 for performing processing of the spectra using a method as disclosed in the present application.

This architecture can be reproduced, so as to juxtapose several detectors of the type described above, to make up an array in one dimension (called a connecting strip) or a two-dimensional array (called a matrix).

Other processing means, for example based on delay line circuits, in particular making it possible to shape the signal, may be provided upstream from the analog/digital converter.

Radiation spectrum refers to a histogram of the amplitudes of the detected pulses, having at least two channels, each channel corresponding to a determined amplitude range. The amplitude of a pulse being proportional to the energy deposited in the detector by an interaction, such a spectrum is also a histogram of the energy for the detected interactions.

During use of the device, a sample of material 100 is arranged between the source and the detector so as, as we will see below, to perform a calibration or, after calibration has taken place, to be characterized.

The means 12 in particular include a computer or a microcomputer or a computer programmed to store and process spectrum data and data to implement a method according as disclosed in the present application, for example transmitted spectrum data I and $I_0$ and/or the coefficient μ(E) or thickness data for the material passed through. The attenuation coefficients $\alpha_1$ and $\alpha_2$ described later may thus also be calculated.

The means 12 or a central unit 16 are programmed to carry out a processing method as disclosed in the present application, by calculating the transmission function data from transmitted spectrum data I and $I_0$. They further have storing means for storing measured data, and for storing data processed using a method as disclosed in the present application. Storing means are also provided for applying the method steps as disclosed in the present application.

All or part of the processing method as disclosed in the present application may be applied using the means 10, these means being able to be a FPGA (Field Programmable Gate Array) or an ASIC (Application Specific Integrated Circuit).

The means 12 may make it possible to control the X radiation source 1, to trigger an emission of radiation and perform one or more measurements using the detector 2. These electronic means 12 may make it possible to perform a synchronous check of the triggering of the radiation source(s) and the detector(s).

These means 12 may also make it possible to perform statistical calculations to implement the inventive method, in particular during the calibration phase. They also make it possible, during the measuring phase, to determine the nature and possibly the thickness of a material to be characterized, as explained below.

Using the means 12, an operator may select one or more parameters to perform these operations.

He/she may also select a number N of energy bands N≥2, from which the attenuation coefficients $\alpha_n$, n≥2 will be able to be calculated, as explained below. Each attenuation coefficient is calculated by applying a statistical quantity or function to the attenuation function in a given energy band. This indicator may for example be the integral or the average of the transmission function in the considered energy band.

When N=2, these energy bands correspond to a so-called low energy zone and a so-called high energy zone, and a first attenuation coefficient $\alpha_1$ is determined, corresponding to the low energy band, and a second transmission coefficient $\alpha_2$, corresponding to the high energy band.

On the screen or the visualization means 17, it is possible to display:
  measured spectra I and $I_0$,
  and/or one or more attenuation and/or representation functions such as one of FIG. 3-6, 8A-8C, or 13-16B,
  the nature and possibly the thickness of a material to be characterized.

From these viewing means, an operator may also define or select the low-energy and high-energy zones used to calculate the coefficients indicated above.

Figure 1B:
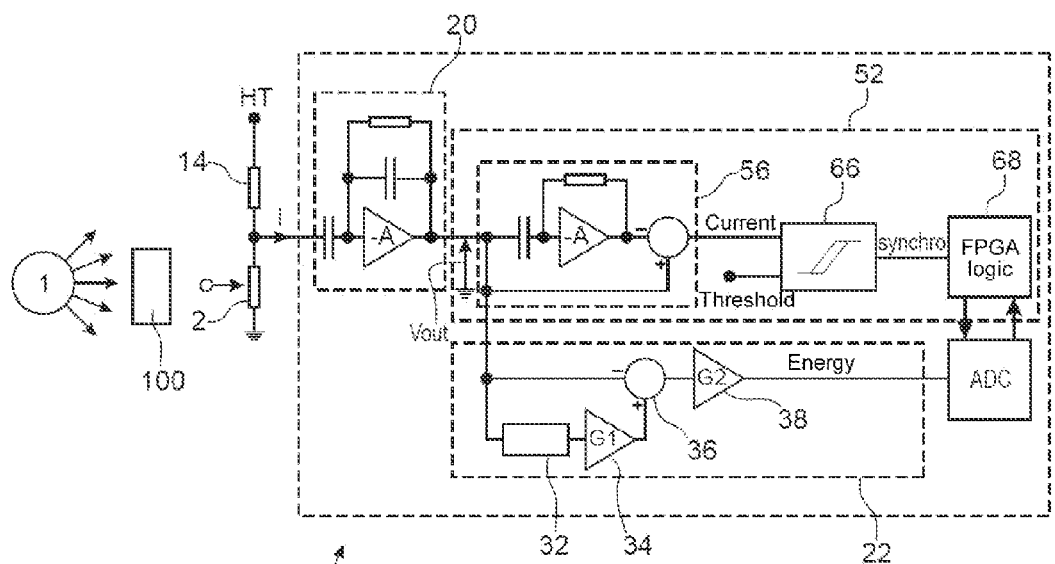

Such a device may also apply a delay line making it possible to shape the pulses in the form of a trapezoid, for example as described in EP 2071722. This device, illustrated in FIG. 1B, primarily includes:
  a charge pre-amplification circuit 20 of the integrator type, able to be connected to the semiconductor detector 2 (the resistance 14 designates a biasing resistance associated with the detector 2),
  a circuit 22 for measuring energy by delay line (having a delay line 32, a first gain 34, a subtractor 36 and a second gain 38), connected at the output of the pre-amplification circuit, and
  a sampler connected at the output of the energy measuring circuit.

It also has a synchronization circuit 52 comprising:
  a circuit 56 for measuring current pulses, connected at the output of the pre-amplification circuit 20 and obtaining the difference between the output and a derivative of the output of the pre-amplification circuit, and
  a discriminating circuit 66 forming a binary signal as a function of the output of the pulse measuring circuit 22, said logic signal controlling the sampling moments of the sampler.

Means such as the means 12 described above may be combined with this circuit to produce a device implementing a method as disclosed in the present application.

Other aspects of this circuit are described in document EP 2071722.

A device as disclosed in the present application makes it possible to perform a measurement of a spectrum I0 of an incident beam: this spectrum can be averaged over a large number of acquisitions so as to minimize the effect of photon noise. This spectrum I0 is the spectrum of the radiation detected by the detector in the absence of material (examined material or sample material) between the source and the detector.

Then, an object 100 to be analyzed is positioned in front of the beam (FIG. 1A, typically a luggage or, more generally, a sample of material to be analyzed) or an object or material 100 that will be used during the calibration of a device.

The spectrum I of the radiation transmitted through this object during the selected period, generally fairly short, and for example between several hundreds of μs and several 100 ms, and generally less than 10 ms or several tens of ms is measured. This spectrum I may or may not be averaged, but preferably, it is not.

Figure 2:
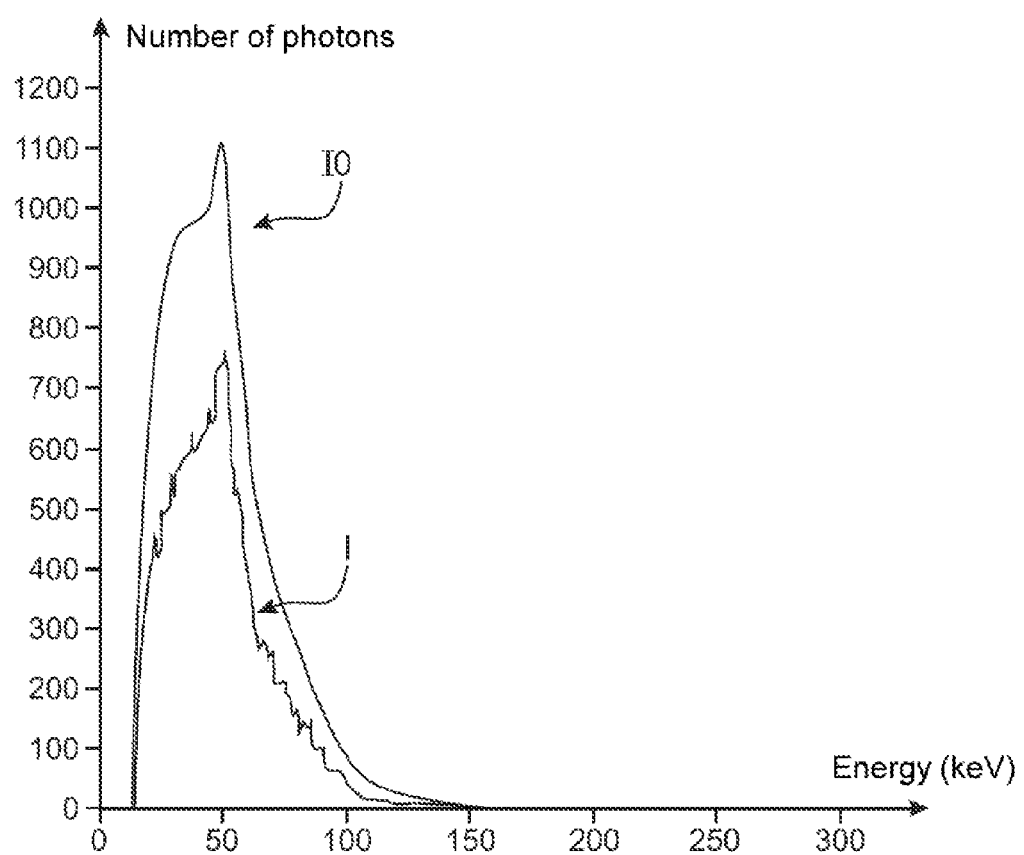
FIG. 2 is an example of spectra of an incident beam before and after transmission through a material.

An example of the measurements thus done is shown in FIG. 2, where two spectra I and I0 are seen.

It will now be recalled that the attenuation function for an object subjected to radiation corresponds to:

$$-\ln\left(\frac{I}{I_0}\right) = \mu(E) \cdot l$$

with:
  Io=Number of incident photons per unit of time,
  I=Number of photons that pass through the material per unit of time,
  μ(E)=Linear attenuation coefficient depending on the energy and the material,
  l=Thickness of the material passed through.

The ratio I/Io (ratio of the number of photons transmitted by the object over the number of photons having entered the object) corresponds to the transmission function of the object and is noted as TR(E).

The implemented system, and in particular the means 12, 16, make it possible to calculate, from the measured transmission function, for each energy channel, the value of $-\ln(I/I_0)=\mu(E).l$. The attenuation function corresponding to the material passed through by the beam is thus obtained. Because of the spectrometric capacities of the sensor, this function is discretized in energy.

For a given material, having, at an energy E, a given linear attenuation coefficient μ(E), the Neperian logarithm of the transmission function varies linearly with the thickness of the material.

Figure 3:
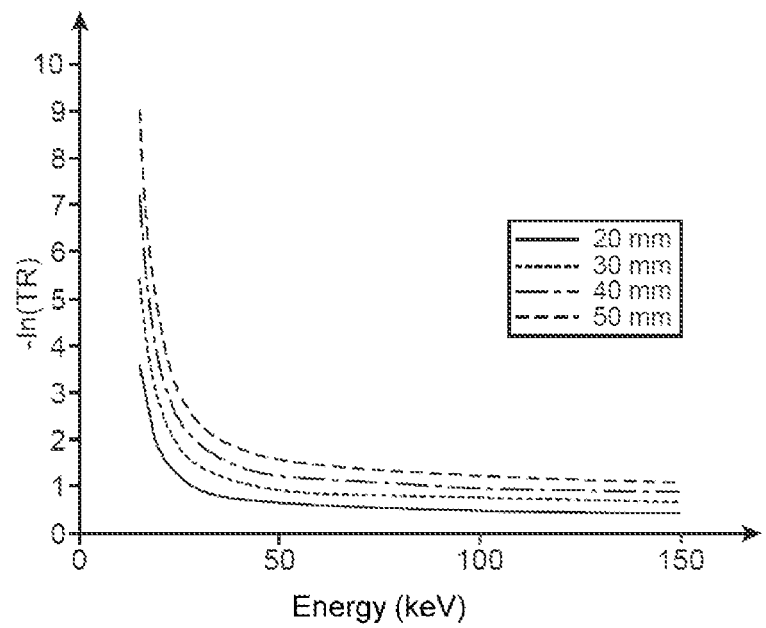
FIGS. 3 and 4 are examples of attenuation functions.

FIG. 3 shows the attenuation functions of a same material (Delrin) at different thicknesses (20 mm, 30 mm, 40 mm, 50 mm). It is shown that the different attenuation functions are indeed proportional to each other.

Figure 4:
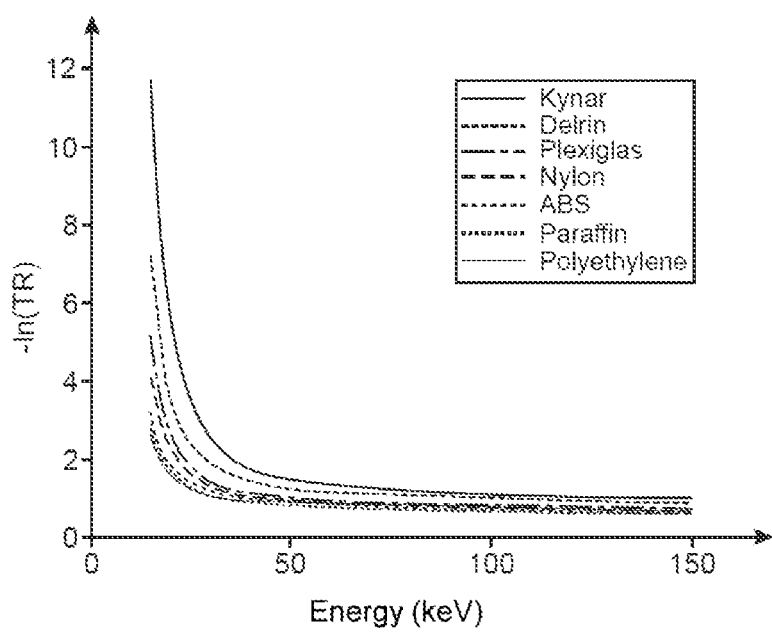

In order to determine in what energy range the attenuation functions make it possible to best discriminate between two different materials (i.e. materials of a different nature), in FIG. 4 are shown the transmission functions of different materials at a same thickness (40 mm).

This figure shows that these functions all have the same general appearance, but that they theoretically make it possible to differentiate between the materials according to the nature of those materials. They are proportional to each other in the high energies (greater than 70 keV), whereas their appearances are better differentiated from each other at low energies (below 70 keV or even 50 keV).

Figure 5A:
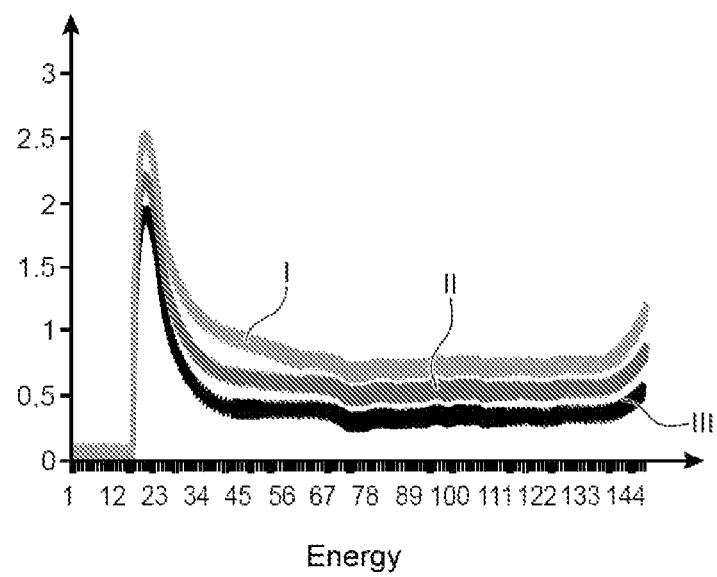
FIGS. 5A-5B illustrate transmission functions averaged over several measurements, low-energy and high-energy selection zones being positioned in FIG. 5B.
Figure 5B:
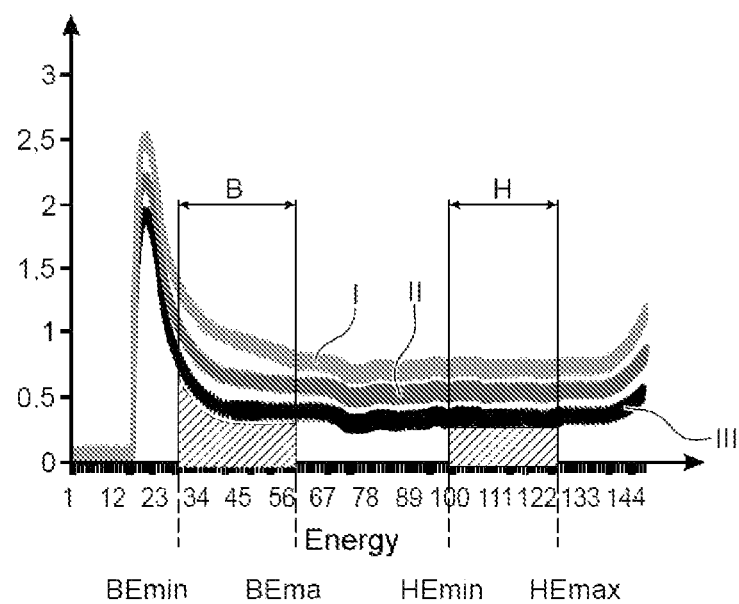

It is possible to produce an average of the results obtained over a certain number of measurements, which makes it possible to reduce their photon noise. In FIG. 5A, an average is thus shown, taken from 100 measurements for three plastic materials with different densities: Teflon (curve I), Delrin (curve II) and polyethylene (curve III).

Delrin is interesting because it has characteristics (density and atomic number) close to those of common explosives.

We shall first describe the case where only two attenuation coefficients $\alpha 1$ and $\alpha 2$ are considered.

We may thus look at two energy bands (N=2), a first so-called low energy band (and limited by two values $BE_{min}$ and $BE_{max}$, see FIG. 5B), and a second so-called high energy band (and limited by two values $HE_{min}$ and $HE_{max}$).

More specifically, it is possible to identify these two zones by one and/or the other of the following criteria. Each of these zones is relatively wide, with a width between 5 keV and 50 keV, preferably between 15 keV and 50 keV. A first zone, called low energy and particularly relevant, is between 10 keV or 20 keV or 22 keV and 40 keV, and a second zone, called high energy, can be chosen between 50 keV and 120 keV, and very advantageously between 54 and 112 keV.

Preferably, each zone does not have disruptions of the electronic noise type (affecting low energies). In particular a zone, at high energies, having excessively low statistics is avoided.

Preferably, these zones are limited to the channels for which the attenuation function does not have an obvious distortion: the extreme channels of the spectrum are therefore avoided.

Still preferably, in a first zone, the attenuation functions behave substantially differently from each other (low energy) while, in the second zone, the attenuation functions are relatively parallel to each other (this is the case at high energy). Therefore, a first zone will be very sensitive, i.e. will vary significantly depending on the nature of the material and/or its thickness, while a second zone will evolve much less than the first zone as a function of the nature of the material and/or its thickness.

It is an operator who will select, for example from one of the criteria described above and using the means 12, 16, 17, the low energy and high energy bands from which the coefficients $\alpha_1$ and $\alpha_2$ will be able to be calculated, as explained below.

In each of these two zones or bands, it is therefore possible to calculate the integral of the attenuation curve relative to the energy variable. But it is also possible to use statistical quantities other than the integral, for example the average.

In the case where the selected statistical quantity is the integral, the calculation of two coefficients is then done, each equal to the energy integral of the attenuation function in each of these two zones. The energy terminals of the low energy zone are noted as $BE_{min}$ and $BE_{max}$. The high energy terminals are noted as $HE_{min}$ and $HE_{max}$.

For example, for polyethylene, the attenuation function of which is noted attPE200:

$$\alpha 1 = \int_{Be\ min}^{Be\ max} attPE200$$

and $$\alpha 2 = \int_{He\ min}^{He\ max} attPE200$$

It is thus possible to calculate two coefficients $\alpha 1$ and $\alpha 2$ as follows:

$$\alpha_1 = \sum_{BE_{min}}^{BE_{max}} -\ln\left(\frac{N(E)}{N_0(E)}\right) \text{ and } \alpha_2 = \sum_{HE_{min}}^{HE_{max}} -\ln\left(\frac{N(E)}{N_0(E)}\right)$$

Practically, these coefficients can be obtained by calculating the attenuation function of the object, then adding this attenuation function on both selected energy ranges.

The same coefficients may be calculated, for Teflon and Delrin for example, and compared with each other for identification.

The two coefficients $\alpha_1$ and $\alpha_2$ (called attenuation coefficients) are calculated from attenuation functions, and this may be done within a short integration time (several ms).

The measured data, as well as the calculated data (and in particular the coefficients $\alpha_1$ and $\alpha_2$) may be stored in the storing means 12, 16 for data processing.

Figure 6:
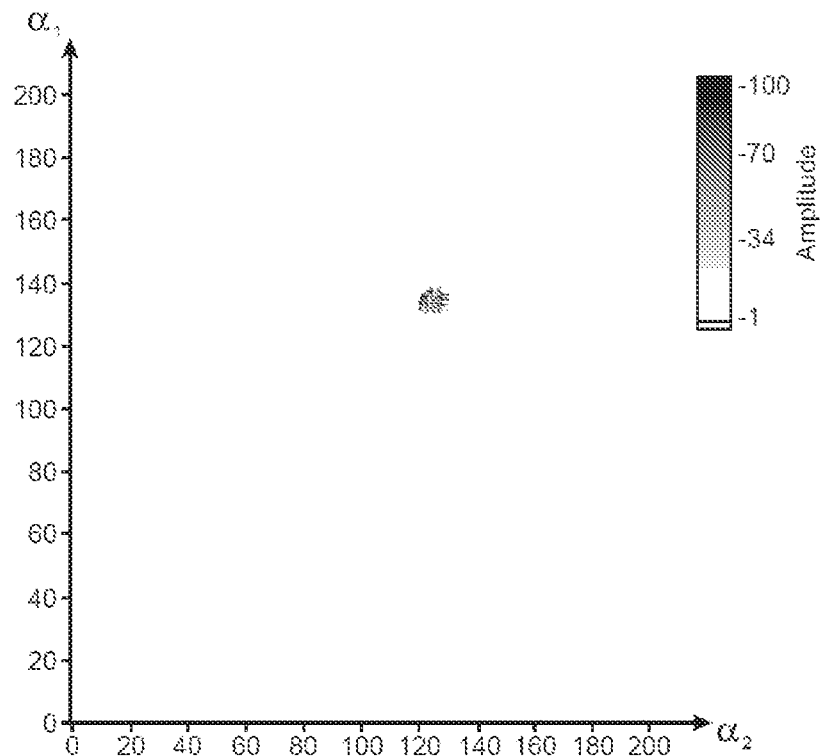
FIG. 6 shows the positioning of a set of measurements in a plane $(\alpha_1, \alpha_2)$.

If, for each measurement corresponding to an integration time, a set of coordinates $(\alpha_1, \alpha_2)$ is shown in a plane, for example for 1,000 successive measurements, a cloud of points is obtained, which have identical or very close coordinates, as shown in FIG. 6.

Consequently, according to this technique, it is possible to select different parameters for the attenuation function, or attenuation coefficients, corresponding to as many energy ranges. It is then possible to compare these parameters to parameters determined from reference materials, with a known nature and thickness. For example, each parameter may be the average of this attenuation function over a determined energy range. Thus, a set of attenuation coefficients $\alpha 1, \ldots \alpha N$ is determined according to the values of the attenuation function of the object in N energy bands. These attenuation coefficients may be determined:

as a function of the attenuation function value in different energy bands, and particularly when a spectrometric detector is used, as a function of the estimate of the attenuation function in the energy band corresponding to a non-spectrometric detector.

Figure 7:
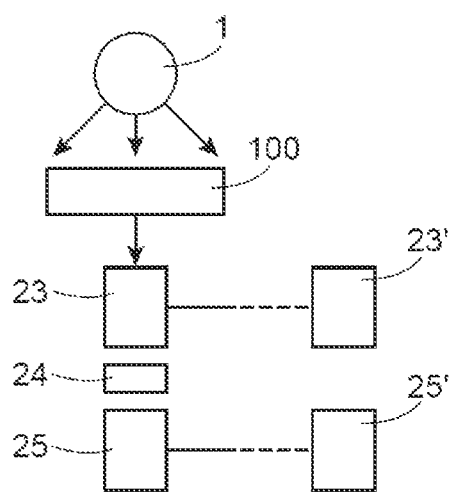
FIG. 7 shows a sandwich-type sensor.

A second embodiment of a sensor which may be used in the present context is shown diagrammatically in FIG. 7.

These are two associated non-spectrometric detectors, this configuration possibly being called a sandwich sensor, having a first detector 23 making it possible to absorb the low-energy (BE) photons, then a filter 24, and a second detector 25, absorbing the high-energy (HE) photons. The detectors 23 and 25 are typically scintillation detectors with photodetectors, for example photodiodes or photomultipliers. During an acquisition, each detector generates a signal depending on the energy deposited by the X radiation interacting in the detector. But these detectors are not able to produce a spectrum of the energy of the X radiation interactions.

Each layer 23, 25 is connected to a photodetector 23', 25' which provides an electric signal whereof the amplitude depends on the energy released in the detector material during the interaction.

The main advantage of such a detector relative to systems with two successive firings is the possibility of acquiring two energies in simultaneous mode spatially and temporally. A spectrometric sensor, like that of FIG. 1A, has the same type of advantage. The drawback of the sandwich sensor is the very poor energy separability (due to an overlap of the BE and HE spectra), and the difficulty of generalizing at more than two energies. Characteristics of an example of a sandwich detector used in the present context are the following: two layers 23, 25 of CsI (with respective thicknesses of 0.3 mm and 5.0 mm) separated by a metal filter 24 (for example 0.7 mm of copper).

The first sensor, placed near the object, delivers a signal produced by the "low energy" component of the radiation, while the second detector, generally larger, and placed behind the front detector along the axis of propagation of the radiation, produces a signal representative of the "high energy" component of the X beam. Thus, a low-energy component and a high-energy component are obtained. This makes it possible, without using spectrometry systems, to obtain a "low energy" component and a "high energy" component.

Means 12, 16, 17 make it possible to process spectra using a method as disclosed in the present application. These means and their functions have already been described above.

More generally, it is possible to use a plurality of detectors, aligned along the axis of a ray, each detector being able to supply a signal depending on the energy deposited in the detector. Dense materials may be inserted between the detectors. Thus, the detector located closest to the object, called the first detector, will produce a signal representative of a low energy, while the detector situated away from the object will produce a signal representative of a high energy. If one limits the number of detectors to two, the "sandwich sensor" described above results. A parameter which may be likened to an attenuation coefficient of the ray is extracted from each signal measured by a detector. The first detector makes it possible to obtain a so-called low-energy coefficient, while the second detector makes it possible to obtain a high-energy coefficient. The measured coefficients are then compared to values obtained on reference materials, which have a known thickness and nature. It is for example possible to place a low-volume detector near the inspected object, and to increase the volume of the detectors as one moves further away from the object. Thus, when N detectors are available, it is possible to extract N attenuation coefficients $\alpha_1, \ldots \alpha_N$, each parameter resulting from the measurement by a detector.

According to still an alternative, a single non-spectrometric detector is used, but the latter is successively exposed to incident radiation having different energies. It is therefore possible, here again, to extract N attenuation coefficients $\alpha_1, \ldots \alpha_N$, each parameter resulting from a measurement done with the same detector, but exposed to an energy different from those at which the other measurements are done.

During use of the device, a sample of material 100 is arranged between the source 1 and this detector, so as to be characterized.

A representation of an acquisition is the measurement or high-energy attenuation coefficient $\alpha_{HE}$ as a function of the measurement or low-energy attenuation coefficient $\alpha_{BE}$. As explained above, an attenuation measurement is calculated by taking the logarithm of the ratio of two measurements of the energy absorbed by the sensor: measurement in the absence of an object, called full flow and done during a calibration phase of the system, divided by that with an object.

Let $N_{BE}(E)$ and $N_{HE}(E)$ be the numbers of energy photons E absorbed respectively by the first detection layer 23 and the second detection layer 25 of the sandwich sensor in the presence of an object 100.

In the absence of an object, they are noted $(N_{BE}(E))_0$ and $(N_{HE}(E))_0$. Thus, for a polychromatic spectrum:

$$\alpha_{BE} = \ln\left(\frac{\int_E E \times (N_{BE})_0(E) dE}{\int_E E \times N_{BE}(E) dE}\right)$$

Similarly:

$$\alpha_{HE} = \ln\left(\frac{\int_E E \times (N_{HE})_0(E) dE}{\int_E E \times N_{HE}(E) dE}\right)$$

Let $\mu(E)$ denote the linear attenuation coefficient of the object examined at energy E and ep its thickness. According to the Beer-Lambert attenuation coefficient:

$N_{BE}(E)(N_{BE})_0 \times \exp(-\mu(E) \times ep)$ and $N_{HE}(E)=(N_{HE})_0 \times \exp(-\mu(E) \times ep)$ In the case of radiation made up of two distinct energy components $E_{BE}$ and $E_{HE}$, the measurements are therefore:

$\alpha_{BE}=\mu(E_{BE}) \times ep$ et $\alpha_{HE}=\mu(E_{HE}) \times ep$

Under these optimal conditions, the coefficients ($\alpha_{BE}$, $\alpha_{HE}$) have the property of being proportional to the thickness of the imaged object. This property is, however, damaged by the spectrum hardening phenomenon related to the polychromatic nature of the radiation emitted by the X tube: the part detected in the second layer 25 lacks its low-energy component, which has been filtered out by the first layer 23.

Let us now consider a radiographic acquisition of an object made up of a single material, characterized by the nature of the material and by its thickness. This acquisition is preferably done using one of the two devices described above. The measurement is then put in the form of a pair of coefficients, i.e. ($\alpha_{BE}$, $\alpha_{HE}$) or ($\alpha_1$, $\alpha_2$) as explained above. These attenuation coefficients are calculated differently with non-spectrometric detectors than with a spectrometric detector, but, irrespective of the type of detector used, they are established from an estimate of the attenuation function in a given energy range.

In general, it is possible to indicate that the measurement is put in the form of a pair of attenuation coefficients ($\alpha1$, $\alpha2$), these data being either the attenuation coefficients obtained using a spectrometric detector, or the coefficients ($\alpha_{BE}$, $\alpha_{HE}$), obtained using the non-spectrometric detectors described earlier.

According to the present teaching, these two coefficients are associated with the most likely material from among a set of a priori materials. The identification criterion used for this detection can be a maximum likelihood criterion.

Figure 9:
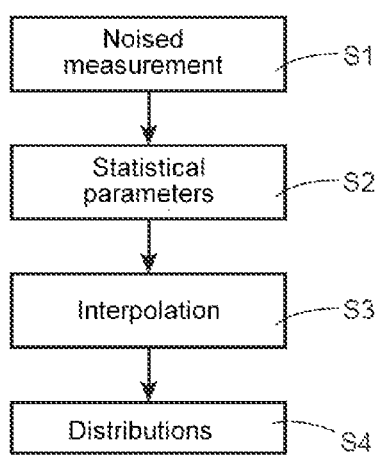

To that end, any measurement is preceded by a calibration, which is shown diagrammatically in FIG. 9 and may be broken down into three main stages:

performance of measurements on known materials (step S1), characterization of the statistical parameters of these measurements (step S2), interpolation of these previously calculated parameters (step S3).

Then, a current measurement can be done, on an unknown material, the results of this measurement allowing a comparison with the calibrated data previously done and a very rapid identification.

Hereinafter, for the sake of simplicity, the method is presented for measurements done with a spectrometric sensor. It may be transposed directly in the case of a sandwich sensor comprising N detectors. In any case, there are N attenuation coefficients ($\alpha_1, \ldots \alpha_N$), with $N \geq 2$.

The calibration steps S1-S3 are first shown.

The calibration makes it possible to build a database for independent productions of the two noised coefficients ($\alpha_1$, $\alpha_2$) if the two-dimensional case is considered.

Figure 10:
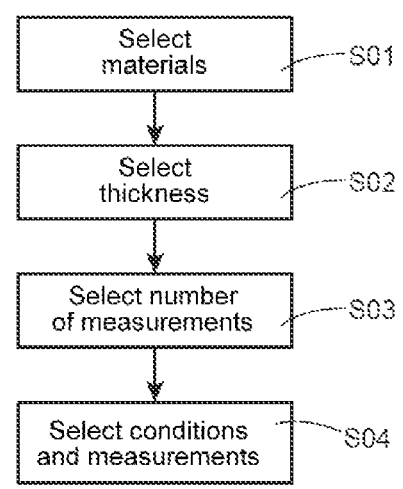

Beforehand, the samples and conditions under which and in which the calibration measurements will be done are determined (diagram in FIG. 10).

Each calibration material, as well as the thicknesses or thickness ranges at or in which each of these will be characterized are selected (steps $S_{01}$, $S_{02}$ of FIG. 10, these steps may be carried out in the opposite order, or simultaneously). Hereinafter, each pair (material, thickness) is identified by a pair of indices (i_mat, i_ep). In other words, each calibration material, for a given thickness of that material, is identified by the pair of indices (i_mat, i_ep).

For each material-thickness pair, a number N_stat of independent measurements is determined (step $S_{03}$). N_stat is typically in the vicinity of 1,000, but, more generally, is selected between 100 and $10^4$ measurements.

One also determines (step $S_{04}$) the conditions under which the calibration measurements are done. Preferably, one selects those of a current acquisition (or "online" acquisition, outside calibration), so that the noise taken into account during the calibration is similar to that affecting the measurements, i.e. with:

a same X radiation fluence rate, same intensity and voltage adjustments of the X generator, same integration times, as under the conditions of a current acquisition.

Figure 11A:
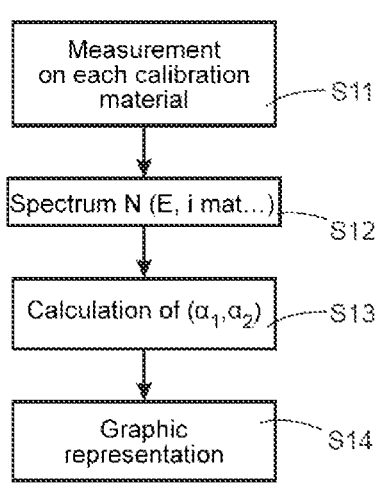

Then, the first step $S_1$ of the calibration strictly speaking is carried out (diagram of FIG. 11A).

Measurements are therefore done (step $S_{11}$) through each of the materials and at the different selected thicknesses or thickness ranges. In other words, N_stat measurements are done on each of the calibration materials, at the different thicknesses selected for each material.

The data resulting from each measurement is converted into a spectrum also identified by the four indices (E,i_mat, i_ep,i_stat) (step $S_{12}$).

For a given material i_mat and thickness i_ep, a measurement among the independent N_stat measurements is referenced by i_stat (0<i_stat≤N_stat). i_stat is the index making it possible to identify a spectrum among the different noised spectra acquired on the same object. In other words, i_stat represents producing noise on the measurement.

For each value of the current index i_stat (0<i_stat≤N_stat), the measured value of the transmission function is converted into two attenuation coefficients ($\alpha_1$, $\alpha_2$) (step $S_{13}$).

For each spectrum N(E,i_mat,i_ep,i_stat), one therefore calculates:

$$\alpha_1(i\_mat, i\_ep, i\_stat) = \sum_{BE_{min}}^{BE_{max}} -\ln\left(\frac{N(E, i\_mat, i\_ep, i\_stat)}{N_0(E)}\right) \text{ and}$$

$$\alpha_2(i\_mat, i\_ep, i\_stat) = \sum_{HE_{min}}^{HE_{max}} -\ln\left(\frac{N(E, i\_mat, i\_ep, i\_stat)}{N_0(E)}\right)$$

The set of spectra may lastly be seen as a four-dimensional quantity, which are:

energy E;

material i_mat;

thickness i_ep; and measurement i_stat.

Figure 8A:
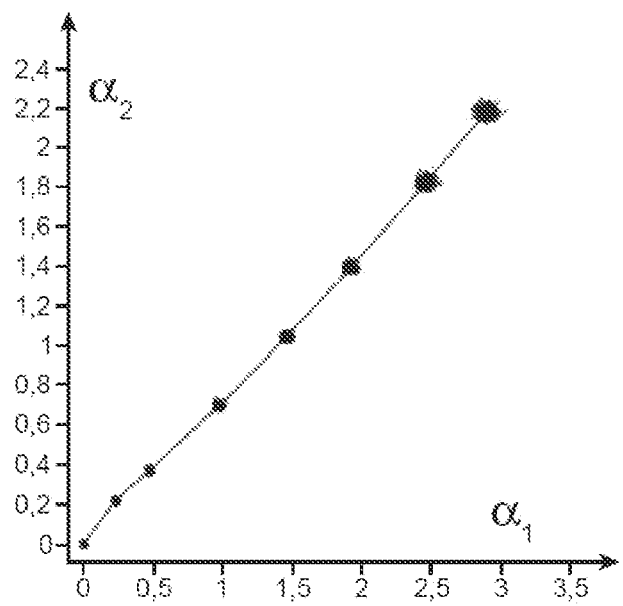
FIGS. 8A-8C show experimental data showing the evolution of coefficients corresponding to the calibration measurements in the case of three materials (with 1,000 measurements per material-thickness pair), FIG. 9 diagrammatically shows the progression of a calibration method as disclosed, FIG. 10 diagrammatically illustrates the progression of preparing for a calibration method as disclosed, FIGS. 11A and 11B each diagrammatically show the progression of a step of a calibration method as disclosed, FIG. 12 diagrammatically shows the progression of a measurement as disclosed.
Figure 8B:
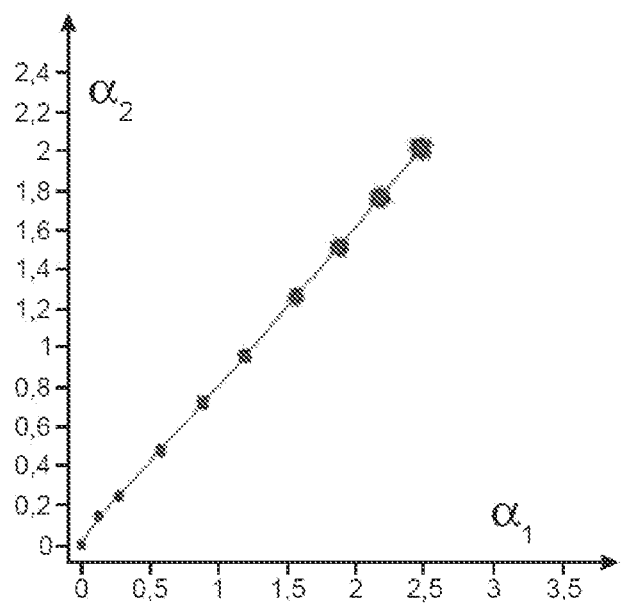
Figure 8C:
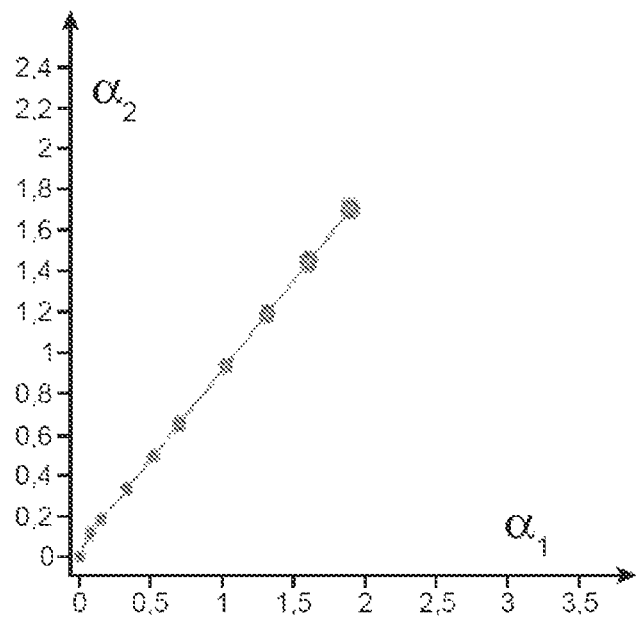

A graphic representation (step $S_{14}$) may then be done, for example on the means 17, like that of FIGS. 8A-8C.

The materials selected for this example are Delrin (FIG. 8B), Polyethylene (FIG. 8C) and Teflon (FIG. 8A) in the following thickness ranges:

0 to 80 mm (in the example: at 0 mm, then 5 mm, then 10, 20, 30, 40, 50, 60, 70, 80 mm), for Delrin, 0 to 100 mm (in the example: at 0 mm, then 5 mm, then 10, 20, 30, 40, 55, 60, 70, 85 and 100 mm), for polyethylene, and 0 to 60 mm (in the example: at 0 mm, then 5 mm, then 10, 20, 30, 40, 50, 60 mm), for Teflon. The acquisitions are done here using a spectrometric sensor.

The clouds of points in the plane ($\alpha_1$, $\alpha_2$) representative of the measurements at the different thicknesses are shown in FIGS. 8A (Teflon), 8B (Delrin), 8C (polyethylene). Each group of points corresponds to the different values of ($\alpha_1$, $\alpha_2$) for the different values of i_stat, the indices i_mat and i_ep (therefore the nature of the material and its thickness) being fixed.

Statistical calculations may then be performed on these measurements from the calibration (step S2 of the calibration method, FIG. 9), for example using the means 12.

More particularly, for each material-thickness pair (i_mat, i_ep), the calculations of the following statistical parameters may be performed on all of the N_stat measurements:

Calculation of the averages of $\alpha_1$ and $\alpha_2$:

$$\mu_1(i\_mat, i\_ep) = moyenne(\alpha_1(i\_mat, i\_ep, :))$$
$$= \frac{1}{N\_stat} \sum_{i\_stat=1}^{N\_stat} \alpha_1(i\_mat, i\_ep, i\_stat)$$

$$\mu_2(i\_mat, i\_ep) = moyenne(\alpha_2(i\_mat, i\_ep, :))$$
$$= \frac{1}{N\_stat} \sum_{i\_stat=1}^{N\_stat} \alpha_2(i\_mat, i\_ep, i\_stat)$$

Calculation of the standard deviations of α1 and α2:

$$\sigma_1(i\_mat, i\_ep) = \text{standard deviation}(\alpha_1(i\_mat, i\_ep, :))$$

$$= \sqrt{\frac{1}{N\_stat - 1} \sum_{i\_stat=1}^{N\_stat} (\alpha_1(i\_mat, i\_ep, i\_stat) - \mu_1(i\_mat, i\_ep))^2}$$

$$\sigma_2(i\_mat, i\_ep) = \text{standard deviation}(\alpha_2(i\_mat, i\_ep, :))$$

$$= \sqrt{\frac{1}{N\_stat - 1} \sum_{i\_stat=1}^{N\_stat} (\alpha_2(i\_mat, i\_ep, i\_stat) - \mu_2(i\_mat, i\_ep))^2}$$

Calculation of the correlation coefficient between α1 and α2:

$$\rho(i\_mat, i\_ep) = \frac{\sigma_{12}(i\_mat, i\_ep)}{\sigma_1(i\_mat, i\_ep)\sigma_2(i\_mat, i\_ep)}$$

With:

$$\sigma_{12}(i\_mat, i\_ep) =$$

$$\sqrt{\frac{1}{N\_stat - 1}} \times \sqrt{\sum_{i\_stat=1}^{N\_stat} \begin{array}{l}(\alpha_1(i\_mat, i\_ep, i\_stat) - \mu_1(i\_mat, i\_ep)) \times \\ (\alpha_2(i\_mat, i\_ep, i\_stat) - \mu_2(i\_mat, i\_ep))\end{array}}$$

It is then possible to perform an interpolation of the statistical parameters (step S3).

This step makes it possible to estimate the same statistical parameters (here: the 5 average statistical parameters µ1 and µ2, standard deviations σ1 and σ2, and coefficient of correlation ρ) for a certain number of thicknesses of the calibration materials. In other words, it involves knowing the statistical parameters for intermediate thicknesses between those measured without using additional measurements.

Figure 11B:
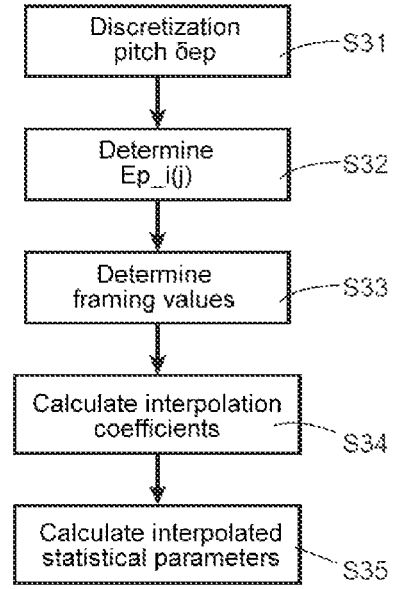

To that end, a thickness discretization pitch is first selected (step $S_{31}$, FIG. 11B). It is noted as δep.

Interpolations (for example of the linear type) are then done in the plane of the variables $(\alpha_1, \alpha_2)$ or $(m_{HE}, m_{BE})$ to calculate the average values, standard deviations and coefficients of correlation between the two variables for the different material-thickness pairs, with this discretization pitch.

For a selected thickness Ep_interp(j_interp) (step $S_{32}$), the two consecutive thicknesses acquired experimentally framing Ep_interp(j_interp) are determined (step $S_{33}$). They verify:

$$Ep(i\_ep, i\_mat) \leq Ep\_interp(i\_interp) \leq Ep(i\_ep+1, i\_mat)$$

For a thickness index i_interp, the associated thickness may be calculated according to the first measured thickness Ep(1,i_mat):

$$Ep\_interp(i\_interp) = Ep(1, i\_mat) + i\_interp \times \delta ep:$$

Two interpolation coefficients are then calculated (step $S_{34}$):

$$C1 = \frac{Ep(i+1) - Ep\_interp(j\_interp)}{Ep(i+1) - Ep(i)}$$

$$C2 = \frac{Ep\_interp(j\_interp) - Ep(i)}{Ep(i+1) - Ep(i)}$$

Lastly, the statistical parameters are calculated (step $S_{35}$) by interpolation between the measurements at the thicknesses which frame the current thickness:

$$\mu_1(i\_mat, j\_interp) = C1 \times \mu_1(i\_mat, i\_ep) + C2 \times \mu_1(i\_mat, i\_ep+1)$$

$$\mu_2(i\_mat, j\_interp) = C1 \times \mu_2(i\_mat, i\_ep) + C2 \times \mu_2(i\_mat, i\_ep+1)$$

$$\sigma_1(i\_mat, j\_interp) = C1 \times \sigma_1(i\_mat, i\_ep) + C2 \times \mu_1(i\_mat, i\_ep+1)$$

$$\sigma_2(i\_mat, j\_interp) = C1 \times \sigma_2(i\_mat, i\_ep) + C2 \times \sigma_2(i\_mat, i\_ep+1)$$

$$\rho(i\_mat, j\_interp) = C1 \times \rho(i\_mat, i\_ep) + C2 \times \rho(i\_mat, i\_ep+1)$$

For a same material, the statistical parameters interpolated between two measurements done at two consecutive thicknesses may evolve linearly with the thickness between these two thicknesses. The validity of this hypothesis depends on the thickness discretization chosen for the calibration step. If the linearity of the system is too greatly disrupted, for example by the effects of stacks and spectrum hardening, the calibration may be refined by selecting a smaller pitch δ'ep than the preceding pitch δep. The interpolation calculations above may then be redone.

An additional step (step $S_4$) makes it possible to determine a statistical distribution associated with each set of measurements for a defined pair (i_mat, i_ep) or for a pair (i_mat, i_interp).

It is assumed that it is possible to adopt the hypothesis of a statistical presence probability distribution, for example a Gaussian distribution.

In other words, the detection probability density for a material-thickness pair in the plane of coefficients $(m_{BE}, m_{HE})$ or $(\alpha_1, \alpha_2)$ is approximated by a statistical distribution, a two-dimensional Gaussian in the cited example. The Gaussian is centered on the calculated average $(\mu_1$ or $\mu_2)$.

Let $\sigma_1$ and $\sigma_2$ be the standard deviations of random variables $\alpha_1$ and $\alpha_2$, respectively, and $\mu_1$ and $\mu_2$ their expected values. The correlation between the two variables is calculated through the coefficient of correlation ρ, defined as follows:

$$\rho(i\_mat, j\_interp) = \frac{\sigma_{12}(i\_mat, j\_interp)}{\sigma_1(i\_mat, j\_interp)\sigma_2(i\_mat, j\_interp)}$$

With:

$$\sigma_{12} = \sqrt{E((\alpha_1(i\_mat, j\_interp) - \mu_1(i\_mat, j\_interp))(\alpha_2(i\_mat, j\_interp) - \mu_2(i\_mat, j\_interp)))}$$

An intermediate variable z is then defined:

$$z_{(i\_mat, j\_interp)}(\alpha_1, \alpha_2) = \frac{(\alpha_1 - \mu_1)^2}{\sigma_1^2} + \frac{(\alpha_2 - \mu_2)^2}{\sigma_2^2} - \frac{2\rho(\alpha_1 - \mu_1)(\alpha_2 - \mu_2)}{\sigma_1 \sigma_2}$$

The probability density is then defined by:

$$f_{(i\_mat, j\_interp)}(\alpha_1, \alpha_2) = \frac{\exp\left[-\frac{z_{(i\_mat, j\_interp)}(\alpha_1, \alpha_2)}{2\sqrt{1 - \rho(i\_mat, j\_interp)^2}}\right]}{2\pi\sigma(i\_mat, j\_interp)\sigma_2(i\_mat, j\_interp)\sqrt{1 - \rho(i\_mat, j\_interp)^2}}$$

In bi-energies, i.e. by implementing the detection with the sandwich sensor of FIG. 7, the calculation is performed in the same way. However, it may be shown that in this case, there is no statistical correlation between the low energy (BE) and high energy (HE) measurements, when these measurements are done from non-spectrometric detectors ($\rho=0$). When the measurements are done using a spectrometric detector, the correlation between the two variables ($\alpha_1$ and $\alpha_2$) may be non-null, in particular when the energy ranges [BEmin–BEmax], [HEmin–HEmax] are superimposed. It is from these ranges, from the attenuation function, that the coefficients $\alpha_1$ and $\alpha_2$ will be determined.

We have assumed the example of a Gaussian statistical distribution, but another type of parametric distribution may be selected (for example of the "normal log" type). One then determines beforehand, during step $S_2$ and step $S_3$, the statistical parameters making it possible to calculate the distribution in question. In the case of a "normal log" type law, they are the same as before: the average $\mu$ and the standard deviation $\sigma$.

Once these calibration steps $S_1$-$S_4$ are carried out, it is possible to proceed with a current measurement for an object or a material 100 (see FIGS. 1A, 1B and 7), the nature of which is unknown. This may, in one example of an application, involve luggage whereof one wishes to know if it contains an explosive-type material (let us recall that, in general, an explosive is close to the characteristics of the so-called "Delrin" material).

Using the data gathered during the calibration phase, the identification of the object may be done very quickly. For example, the irradiation by the source 1 has a length or a duration between 3 ms and 30 ms, and the processing time is shorter than 1 ms or in the vicinity of one ms.

Figure 12:
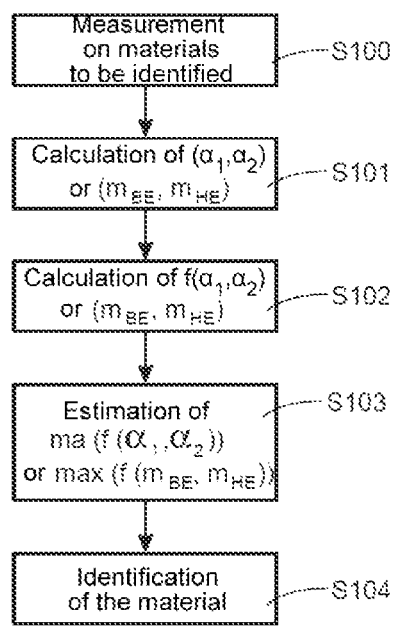
Figure 13:
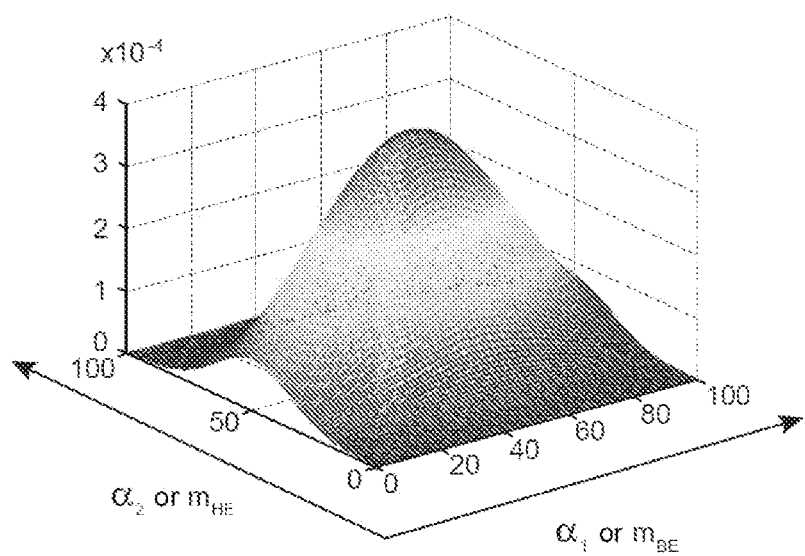
FIG. 13 shows a Gaussian distribution of the coefficients representative of the set of noised measurements for an object-thickness pair, FIG. 14 diagrammatically illustrates a detection of Delrin among a set of three materials (polyethylene, Delrin and Teflon)

This measurement phase will be described relative to FIG. 12.

To that end, the source 1 is triggered, its ray passes through the object 100 to be identified, and is received by the detector 2 or 23-25. The source is continuous here. This is step $S_{100}$ of FIG. 12.

The means 4-16, 23', 25' then make it possible to calculate the coefficients ($\alpha_1, \alpha_2$) or ($m_{HE}, m_{BE}$) (step $S_{101}$), from transmission data calculated in the same energy bands as for the acquisitions done during the calibration.

The values thus calculated will make it possible to determine the values of the probability densities at the measurement point for the different calibration materials at the different interpolated thicknesses. In other words, one calculates (step $S_{102}$), for example from two attenuation coefficients ($\alpha_1, \alpha_2$), the values of the different functions $f_{(i\_mat, j\_interp)}$ or $f_{(i\_mat, j)}$ at point ($\alpha_1, \alpha_2$).

One then estimates (step $S_{103}$) the distribution for which the value of f is greatest. For example, the computer means 16 will make it possible to perform this identification of the maximum value.

The identification of the material (step $S_{104}$) is then based on the result of this identification of the maximum value: the estimated material $i\_mat\ est$ as well as its thickness, $j\_int\ erp\_$ are given by the highest probability density at the measuring point:

$$(i\_mat\_estimé, j\_interp\_estimé) = \underset{i\_mat, j\_interp}{\mathrm{argmax}}\ (f_{(i\_mat, j\_interp)}(\alpha_1, \alpha_2))$$

Figure 14:
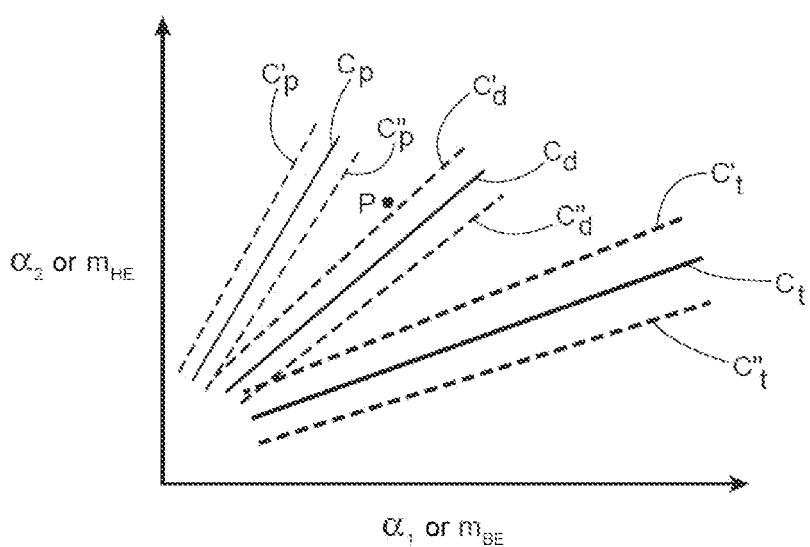

As an example, FIG. 14 schematizes the detection of an a priori of three materials. In this specific case, the values of the probability densities of the three materials are compared at the measuring point P (defined by the pair ($\alpha_1, \alpha_2$) or ($m_{BE}, m_{HE}$); the detected material is then Delrin.

For a same material, the apices of the probability distributions are aligned on the line $C_t$ for Teflon, on the line $C_d$ for Delrin and $C_p$ for polyethylene.

The lines $C'_t$ and $C''_t$ ($C'_d$ and $C''_d$, $C'_p$ and $C''_p$, respectively) show the values of the probability densities at, for example, 5% of the maximum value of the corresponding probability density curve.

An alternative of the inventive method will now be described (so-called "discrete identification method" alternative).

This alternative uses an additional calibration step.

During this additional step, the variables ($\alpha_1, \alpha_2$) are discretized in $N_1$ and $N_2$ values, respectively, so as to cover the measuring space. Typically, each of the values $N_1$ and $N_2$ is of order of magnitude $10^3$ or more, it is for example between 100 and a few million. In this way, it is possible to determine $N_1$ discrete values $\alpha_1$, and it is possible to determine $N_2$ discrete values of $\alpha_2$.

For each material, a mapping of the probability densities is then done:

for each pair of values ($\alpha_1(i), \alpha_2(j)$), with $1 \leq i \leq N_1$ and $1 \leq j \leq N_2$, the probability densities $f_{(i\_mat, j\_interp)}(\alpha_1, \alpha_2)$ of the different thicknesses (indexed by j_interp) are calculated and compared, each pair of values ($\alpha_1(i), \alpha_2(j)$) is assigned a material nature and a thickness. They are defined by the two indices i_mat and j_interp following the equation:

$$[i\_mat(\alpha_1(i), \alpha_2(j)), j\_interp(\alpha_1(i), \alpha_2(j))] = \underset{i\_mat, j\_interp}{\operatorname{argmax}} (f_{(i\_mat, j\_interp)}(\alpha_1(i), \alpha_2(j)))$$

Thus, to each point of the space $(\alpha_1(i), \alpha_2(j))$, with $1 \leq i \leq N_1$ and $1 \leq j \leq N_2$ corresponds a material i_mat and its thickness i_ep satisfying $$\underset{i\_mat, j\_interp}{\operatorname{argmax}} (f_{(i\_mat, j\_interp)}(\alpha_1(i), \alpha_2(j)))$$

The advantage of this solution is that when the coefficients $(\alpha_1, \alpha_2)$ are subsequently measured, a material and a thickness, which are the material and thickness data previously associated with the pair of discrete values $(\alpha_{1(i)}, \alpha_{2(j)})$, closest to the pair of measured values $(\alpha_1, \alpha_2)$, are directly affected.

Figures 15A, 15B, 15C:
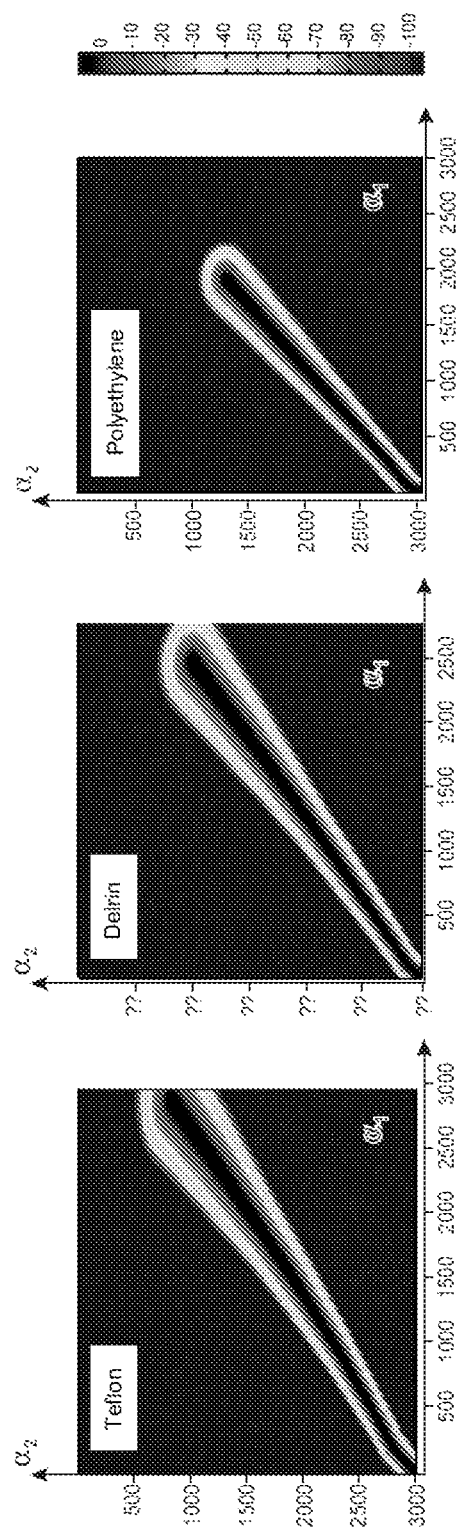
FIGS. 15A-15C illustrate the evolution of probability densities of three materials in the space of the coefficients (α1, α2), from experimental data shown in FIGS. 8A-8C, FIGS. 16A-16B are an example of an embodiment of the identification method with a luggage screening device as disclosed and a comparison of a counting image (FIG. 16A) done on the same system and from the same acquisition data.

Using the previous example of three materials, i.e. Delrin, Polyethylene and Teflon, in the thickness ranges [0-80 mm], [0-100 mm] and [0-60 mm]. The thickness discretization pitch is set to 0.1 mm. FIGS. 15A-15C show the probability densities in the plane $(\alpha_1, \alpha_2)$ for the three materials.

If a measurement is done on an object or a material 100 whereof the nature is unknown, it is possible to calculate, as explained above, the pair of values $(\alpha_1, \alpha_2)$ from transmitted X radiation data.

The closest discrete value of $(\alpha_1(i), \alpha_2(j))$ of the measurement $(\alpha_1, \alpha_2)$ is then estimated. The probability density of the different materials is read on the pre-calculated mappings. The identified material is that which has the highest probability density, in other words the material i_mat_est for which it reaches the maximum $$\underset{i\_mat}{\max}(F_{i\_mat}(\alpha_1, \alpha_2)).$$

The preceding reasoning may be used to determine the material i_mat and the thickness i_ep.

The advantage of this method relative to the previous one is that it requires less "online" computing time for identification, this step being reduced to the density readings on the mappings of the different materials and the comparison of the values.

However, it has a drawback, i.e. the need to store more data in memory (all of the mappings of the different materials), in particular if one determines not two coefficients ($\alpha 1, \alpha 2$), but N coefficients ($\alpha 1, \alpha 2 \ldots \alpha N$), N being able to exceed 10, or even 100. Another drawback is related to the discretization pitch associated with each coefficient.

To increase the accuracy of the mappings, it is possible to refine the discretization of the coefficients ($\alpha 1, \alpha 2$) and therefore increase the volume of useful data.

This alternative may also be implemented using means 12, 16, 17 of a device as disclosed in the present application. Here again, the measured data and the calculated data may be stored in memory, in order to perform the other desired processing or graphic representations.

Until now, we have described an embodiment in which one distinguishes two energy bands of the transmission function, each band making it possible to define a transmission coefficient $\alpha i$, $1 \leq i \leq 2$.

But it is possible to determine N attenuation coefficients $\alpha i$, $1 \leq i \leq N$ and N being able to be $>2$, each coefficient $\alpha i$ being determined from a statistical quantity, for example the integral, applied to an energy band of the energy spectrum of the transmission function.

It is then possible to represent this measurement in a space with N dimensions, each axis of this space then representing the values of a transmission coefficient $\alpha i$. Thus, each measurement has a corresponding point in this space with N dimensions, the coordinates of which are $(\alpha 1, \alpha 2, \ldots \alpha N)$.

This embodiment may be implemented using the same means described above, relative to FIGS. 1A, 1B, 7.

The expression of a Gaussian probability density relative to N variables $(\alpha 1, \alpha 2, \ldots \alpha N)$ is:

$$f(\vec{\alpha}) = \frac{1}{(2\pi)^{N/2} \cdot \sqrt{|\Sigma|}} \cdot e^{-\frac{1}{2}(\vec{\alpha}-\vec{\mu})\sum^{-1}(\vec{\alpha}-\vec{\mu})}$$

The vector $\vec{a}$ corresponds to a column vector with N variables $\alpha_k$, the vector $\vec{\mu}$ being defined subsequently.

$$\vec{\alpha_P}: \begin{bmatrix} \alpha_1 \\ \alpha_2 \\ \ldots \\ \alpha_N \end{bmatrix}$$

In a first step, the Gaussian probability densities are calculated.

For each cloud of points, corresponding to a reference material j with thickness i, a large number of measurements is done, making it possible to determine, upon each measurement, N coefficients $\alpha_{ijkl}$ for which:

i designates the nature of the material, j designates the thickness of the material, k designates the $k^{th}$ transmission coefficient $\alpha_k$ (1<k<N), l designates one measurement among the large number of measurements done, with 1<l<L, L is several hundred or thousand, for example between 100 and 5,000: L represents the number of measurements done with a same material having thickness j and nature i.

In other words, for a same material (i, j), LN coefficients $\alpha_{ijkl}$ are obtained, ordered in L vectors $\alpha_p$.

Once these L vectors are obtained, statistical parameters are estimated relative to a normal probability density, and in particular:

the average, allowing the coordinates of the center of the cloud in each of the dimensions. The vector is then obtained, which may be called $\alpha^0$:

$$\alpha^0: \begin{bmatrix} \alpha_1^0 \\ \alpha_2^0 \\ \ldots \\ \alpha_N^0 \end{bmatrix}$$

where N is the number of dimensions and 0 indicates the coordinate of the center of the cloud. This vector may also be noted as:

$$\vec{\mu} : \begin{bmatrix} \mu_1 \\ \mu_2 \\ ... \\ \mu_N \end{bmatrix};$$

the variance-covariance matrix $\Sigma$, which assumes the following form:

$$\sum = \begin{bmatrix} (\sigma_{\alpha_1})^2 & \sigma_{\alpha_1,\alpha_2} & \sigma_{\alpha_1,\alpha_3} & ... & \sigma_{\alpha_1,\alpha_N} \\ \sigma_{\alpha_2,\alpha_1} & (\sigma_{\alpha_2})^2 & ... & ... & ... \\ \sigma_{\alpha_3,\alpha_1} & & \ddots & & \\ \vdots & & & \ddots & ... \\ \sigma_{\alpha_N,\alpha_1} & ... & ... & ... & (\sigma_{\alpha_N})^2 \end{bmatrix}$$

wherein:

$(\sigma_{\alpha 1})^2$: represents the variance of the coefficient $\alpha_1$ (1st transmission coefficient) for the L performances (for example, if the cloud is made up of 2,000 points (=2,000 spectra acquired), then L=2000, and the variance of $\alpha_1$ is calculated on these 2,000 points). This is therefore a squared standard deviation.

$\sigma_{\alpha 1 \alpha 2}$ represents the covariance coefficient between $\alpha_1$ and $\alpha_2$. The covariance corresponds to a measurement of the dependence of two variables on each other. Thus, two variables with a non-zero covariance are dependent.

It is possible to note, in light of the formula below, that:

$$\sigma_{\alpha 1 \alpha 2} = \sigma_{\alpha 2 \alpha 1}$$

The covariance is calculated as:

$$\sigma_{\alpha_1,\alpha_2} = \sum_{i=1}^{L} \frac{(\alpha_1^i - \alpha_1^0) \cdot (\alpha_2^i - \alpha_2^0)}{L}$$

wherein:

$\alpha_N^i$ represents the coefficient $\alpha$ in the dimension N of the acquired spectrum number i, L represents the number of spectra acquired (=number of points of the cloud), $\alpha_N^0$ represents the average of the coefficient $\alpha$ in the dimension N on the M acquired spectra. This average may also be noted as $\mu N$.

The calculation of the correlation between two variables uses the covariance:

$$\rho_{\alpha_1,\alpha_2} = \frac{\sigma_{\alpha_1,\alpha_2}}{\sigma_{\alpha_1} \cdot \sigma_{\alpha_2}}$$

In this way, if two coefficients are decorrelated, this means that their covariance is null, and therefore only the diagonal of the matrix $\Sigma$ remains, i.e. the variance of each of the coefficients. All of the other coefficients are null.

Obtaining the vector of average values and the covariance matrix makes it possible to define a Gaussian probability density $f_{ij}$ depending on the material of nature i and thickness j.

$$f_{ij}(\vec{\alpha}) = \frac{1}{(2\pi)^{N/2} \cdot \sqrt{|\Sigma|_{ij}}} \cdot e^{-\frac{1}{2}(\vec{\alpha}-\vec{\mu_{ij}})^T \cdot \sum_{ij}^{-1} \cdot (\vec{\alpha}-\vec{\mu_{ij}})}$$

$\Sigma ij$ corresponds to the covariance matrix obtained using this configuration (material i thickness j) and the vector $\mu_{ij}$ corresponds to the vector bringing together the N average values $\mu k$ obtained during the calibration step described earlier for each band of energy k ($1 \leq k \leq N$), N being the number of relevant transmission or attenuation coefficients.

The vector $\vec{\alpha}$ represents N transmission or attenuation coefficients $\alpha_k$ measured in each band of energy k. It is recalled, as described earlier, that, by transmission or attenuation coefficient, are meant coefficients obtained from the comparison between the radiation measurements with and without the object between the radiation source and the detector(s).

In a second step, an interpolation of Gaussians is done.

Two probability densities $fij_1$ and $fij_2$ corresponding to a same material, but two different thicknesses $j_1, j_2$, are interpolated in order to obtain a probability density $fij_3$, with $j_1 < j_3 < j_2$.

The interpolation may be linear: the matrix $\Sigma ij_3$ is obtained by interpolating each element of the matrices $\Sigma ij_1$ and $\Sigma ij_2$, term by term and linearly.

The diagonal corresponds to a linear interpolation of the variance, and the other elements to a linear interpolation of the covariance.

The same process is used to obtain the vector $\mu_{ij3}$ obtained by interpolation of the vectors $\mu_{ij1}$ and $\mu_{ij2}$ term by term.

By repeating these interpolations for a large number of thicknesses of a same material j, probability densities $f_{ij}$ are obtained with j varying from $j_{min}$ (minimum thickness) to $j_{max}$ (maximum thickness).

It is of course possible to renew steps 1 and 2 for different materials i.

In a second step, a measurement is done using the calibration done:

- a measurement of N attenuation coefficients $\alpha k$ is done, and a vector $\vec{\alpha}$ is obtained,
- the functions $f_{ij}$ previously established for the set of M calibrated materials i (these may be called candidate materials, indexed by variable i with $1 < i < M$), and the set of thicknesses j corresponding to these calibrations, with, for each material i, $j_{min,i} < j < j_{max,i}$ where $j_{min,i}$ is the minimum calibrated thickness of the material i and $j_{max,i}$ is the maximum calibrated thickness of the material i.

The unknown material nature and thickness are determined and correspond respectively to the indices i and j of the probability density $f_{ijmax}$, such that $fijmax(\vec{\alpha}_P) = \max\lfloor fij(\vec{\alpha}_P) \rfloor$, with $1 < i < M$, and, for $j_{min,i} < j < j_{max,i}$.

The present teaching makes it possible to adapt a multi-energy radiography system to the detection of explosives during continuous luggage checks.

It is therefore possible to produce, in particular, a luggage testing device based on the use of a spectrometric sensor.

Figure 16A:
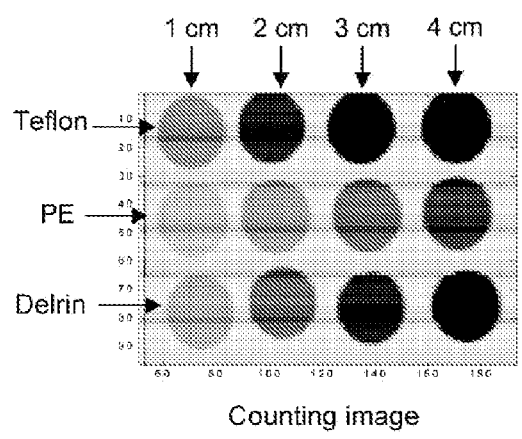
Figure 16B:
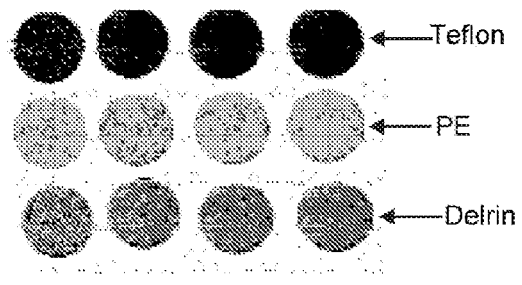

FIGS. 16A, 16B show the results obtained on objects with different thicknesses and made of Teflon, Polyethylene and Delrin.

The X ray generator operates at 120 kV, at 2 million photons per pixel per second. The detector is of the CdTe, surface type, perpendicular to the radiation, 800*800 μm and 3 mm deep, 25 per acquisition, a strip of 16 pixels being moved in both directions to obtain an image.

These figures show the capacities to discriminate explosives relative to common plastics. In fact, Delrin is representative, in terms of density and effective atomic number, of the majority of solid explosives, made up of C, H, O, N atoms.

The "counting" image (FIG. 16A) does not make it possible to perform the identification because the two main characteristics of an object, i.e. its thickness and its composition, cannot be dissociated in radiography. The image of FIG. 16A is a radiographic image (the integral of the attenuation function on all of the considered energies is then determined).

$$pixelvalue = -\ln \frac{\int_{Emin}^{Emax} N(E)dE}{\int_{Emin}^{Emax} N_0(E)dE}$$

The implementation of the identification method makes it possible to create a so-called identification image (FIG. 16B), which associates each pixel with a material nature, regardless of its thickness.

In each of FIGS. 16A, 16B, the top four images correspond to Teflon, the middle four images correspond to polyethylene, and the bottom four to Delrin.

In the case of FIG. 16A, in the upper part, the thicknesses of the measured materials are indicated (successively: 1 cm, 2 cm, 3 cm, 4 cm) (the same thicknesses are used for FIG. 16B).

According to another embodiment, not only conditional probability densities $f_{ij}$ corresponding to a material of nature i and thickness j are used but presence probabilities of a material of nature i and thickness j knowing of a measurement. Also, for each material and each thickness of the calibration base, the pair (material, thickness) will be determined, maximizing not the probability density associated with this material, thickness pair but a probability in order that, knowing of a measurement represented by a vector $\vec{\alpha}$, the investigated material (mat) is the material i and that its thickness (ep) is the thickness j.

It is recalled that the measurement vector $\vec{\alpha}$ corresponds to N attenuation or transmission coefficients $\alpha_k$, each attenuation or transmission coefficient being associated with a band of energy k (1≤k≤n).

Such a conditional probability may be noted as $$p_{\vec{\alpha}}(mat = i \cap ep = j)$$

As Bayes theorem is known, it is possible to write $$p_{\vec{\alpha}}(mat = i \cap ep = j) = p_{mat=i \cap ep=j}(\vec{\alpha}) \cdot \frac{p(mat = i \cap ep = j)}{p(\vec{\alpha})}$$

It will now be shown how each term of the second part of the equation may be obtained.

$p(\vec{\alpha})$=probability of obtaining the measurement $\vec{\alpha}$. It is independent of the nature of the material (i) and of the associated thickness (j).

Thus, it is possible to write $$p_{\vec{\alpha}}(mat = i \cap ep = j) \propto p_{mat=i \cap ep=j}(\vec{\alpha}) \cdot p(mat = i \cap ep = j)$$

The term ∝ designates proportionality
p(mat=i∩ep=j) is the probability that the measured material is the material of nature i and thickness j.
If p(mat=i) designates the probability that the measured material is of nature i and,
if p(ep=j/mat=i) designates the probability that the thickness of the material is j, knowing that the nature of the material is i, then $p(mat=i \cap ep=j) = p(mat=i) \cdot p(ep=j/mat=i)$ therefore $$p(mat = i \cap ep = j) = \frac{1}{N_{mat}} \cdot \frac{1}{N_{ep}^i}$$

With Nmat=number of natures of materials which may be measured, i.e. the number of natures of materials having been subject to calibration.

$N_{ep}^i$ is the number of discrete thicknesses which a given material i may assume. For example, for a given material i, $N_{ep}^i$ is equal to the number of thicknesses interpolated between the minimal thickness (for example 0) and the maximum thickness at which a calibration is made.

Thus, p(mat=i∩ep=j) may be calculated.

Knowing that, for the different energy bands, the probabilities of measuring each term $\alpha(k)$ of the vector $\vec{\alpha}$ are independent, it is possible to write $$p_{mat=i \cap ep=j}(\vec{\alpha}) = \prod_{k=1}^{N} p_{mat=i \cap ep=j}(\alpha(k))$$

Each term $p_{mat=i \cap ep=j}(\alpha(k))$ may be made explicit as follows:

$$p_{mat=i \cap ep=j}(\alpha(k)) = \int_{\alpha(k)_{min}}^{\alpha(k)_{max}} \frac{1}{\sqrt{2\pi}\,\sigma_{mat=i,ep=j}(k)} \cdot \exp\left(-\frac{1}{2}\left(\frac{x - <\mu_{mat=i,ep=j}(k)>}{\sigma_{mat=i,ep=j}(k)}\right)^2\right) dx$$

$\mu_{mat=i,\,ep=j}(k)$ and $\sigma_{mat=i,ep=j}(k)$ respectively designate the average $\mu_{ij}(k)$ and the standard deviation $\sigma_{ij}(k)$ mentioned earlier, which may be obtained by calibration, from a series of transmission or attenuation coefficients $\alpha_{ij}(k)$ obtained by conducting several measurements on a material of nature i and thickness j.

The limits of the integral $\alpha(k)min$, $\alpha(k)max$ are defined as indicated below.

It is known that I(k) corresponds to the signal measured by the sensor in the energy band Ek, while the examined object is located between the radiation source and the sensor. In other words, I corresponds to the spectrum of the radiation transmitted by the object. Now:

$I(k)-1 < I(k) < I(k)+1$

Let f be the function, computed from I, comparing the transmitted spectrum I with the radiation spectrum $I_0$ of the source, f may be an attenuation function or a transmission function.

When f is an increasing function, for example when $$f(I(k)) = \left[\frac{I(k)}{I_0(k)}\right],$$

which corresponds to the transmission function, then $$f(I(k)-1) \leq f(I(k)) \leq f(I(k)+1)$$

When f is a decreasing function, for example when $$f(I(k)) = -\ln\left[\frac{I(k)}{I_0(k)}\right],$$

which corresponds to the attenuation function, then $$f(I(k)+1) \leq f(I(k)) \leq f(I(k)-1)$$

In the following, we shall consider that f(I(k)) is an attenuation function.

The preceding equation becomes:

$$p_{mat=i \cap ep=j}(\alpha(k)) =$$

$$\int_{f(I(k)+1)}^{f(I(k)-1)} \frac{1}{\sqrt{2\pi}\, \sigma_{mat=i,ep=j}(k)} \cdot \exp\left(-\frac{1}{2} \cdot \left(\frac{x - <\mu_{mat=i,ep=j}(k)>}{\sigma_{mat=i,ep=j}(k)}\right)^2\right) dx$$

and therefore, $$p_{mat=i \cap ep=j}(\vec{\alpha}) =$$

$$\prod_{k=1}^{N} \int_{f(I(k)+1)}^{f(I(k)-1)} \frac{1}{\sqrt{2\pi}\, \sigma_{mat=i,ep=j}(k)} \cdot \exp\left(-\frac{1}{2} \cdot \left(\frac{x - <\mu_{mat=i,ep=j}(k)>}{\sigma_{mat=i,ep=j}(k)}\right)^2\right) dx$$

The retained material-thickness pair (i,j) is the one which maximizes $$p_{\vec{\alpha}}(mat = i \cap ep = j),$$

which amounts to stating that it maximizes the expression $$p_{\vec{\alpha}}(mat = i \cap ep = j) \propto p_{mat=i \cap ep=j}(\vec{\alpha}) \cdot p(mat = i \cap ep = j)$$

With:

$$p(mat = i \cap ep = j) = \frac{1}{N_{mat}} \cdot \frac{1}{N_{ep}^i}$$

and $$p_{mat=i \cap ep=j}(\vec{\alpha}) =$$

$$\prod_{k=1}^{N} \int_{f(I(k)+1)}^{f(I(k)-1)} \frac{1}{\sqrt{2\pi}\, \sigma_{mat=i,ep=j}(k)} \cdot \exp\left(-\frac{1}{2} \cdot \left(\frac{x - <\mu_{mat=i,ep=j}(k)>}{\sigma_{mat=i,ep=j}(k)}\right)^2\right) dx$$

Of course, when the function f is an increasing function, $$p_{mat=i \cap ep=j}(\vec{\alpha}) =$$

$$\prod_{k=1}^{N} \int_{f(I(k)+1)}^{f(I(k)-1)} \frac{1}{\sqrt{2\pi}\, \sigma_{mat=i,ep=j}(k)} \cdot \exp\left(-\frac{1}{2} \cdot \left(\frac{x - <\mu_{mat=i,ep=j}(k)>}{\sigma_{mat=i,ep=j}(k)}\right)^2\right) dx$$

Let us note that for determining, $$p_{mat=i \cap ep=j}(\alpha(k)) =$$

$$\int_{f(I(k)+1)}^{f(I(k)-1)} \frac{1}{\sqrt{2\pi}\, \sigma_{mat=i,ep=j}(k)} \cdot \exp\left(-\frac{1}{2} \cdot \left(\frac{x - <\mu_{mat=i,ep=j}(k)>}{\sigma_{mat=i,ep=j}(k)}\right)^2\right) dx$$

the error function erf may be used.

$$\boxed{\int_a^b \frac{1}{\sqrt{2\pi}\,\sigma} \cdot \exp\left(-\frac{(x-x_0)^2}{2 \cdot \sigma^2}\right) dx = \frac{1}{2}\mathrm{erf}\left(\frac{b-x_0}{\sqrt{2}\,\sigma}\right) - \frac{1}{2}\mathrm{erf}\left(\frac{a-x_0}{\sqrt{2}\,\sigma}\right)}$$

Thus, in this embodiment, from obtained calibration data $\mu_{ij}(k)$, $\sigma_{ij}(k)$, for different energy bands $E_k$, from known reference materials of nature i and thickness j, a conditional probability may be established which is associated with a material of thickness i and of nature j, when a series of transmission or attenuation coefficients $\alpha(k)$ are measured, coefficients, which may be represented as a vector $\vec{\alpha}$, the term k are designating the energy band of an attenuation, or transmission function, more generally, a function comparing the radiation transmitted by the object I with the radiation produced by the source $I_0$, this comparison function being discretized in energy.

Thus, by measuring such transmission coefficients on an unknown material, it is possible to estimate its nature and/or its thickness.

This conditional probability may be established according to probability densities, for example Gaussian functions, obtained by conducting measurements on reference materials of known nature and thickness.

The nature i and/or the thickness j of the examined material correspond to the pair of parameters (i,j) which maximize this conditional probability.

Irrespective of the embodiments described in this application, it is possible to determine:

the thickness and the nature of an examined material,
or, when the nature of the examined material is known, only its thickness;
or when the thickness of the examined material is known only its nature.

The invention claimed is:

1. A calibration method for a device for identifying an unknown material using X-rays, the method comprising:

a) determining at least one calibration material (i) and, for each calibration material, at least one calibration thickness (j) of the respective material;

b) measuring, for each of the calibration materials and for each of the determined calibration thicknesses, N attenuation or transmission coefficients $\alpha_K$ for X radiation, with N≥2;

c) setting up a vector $\vec{\alpha}_P$, said vector representing N attenuation or attenuation coefficients $\alpha_K$;

d) repeating operations b) and c), with said calibration material, so that L vectors $\alpha_p$ are obtained, L representing the number of measurements performed with a same calibration material having material i and thickness j;

e) calculating statistical parameters from said L vectors $\alpha_p$; and f) determining or calculating, from said statistical parameters, a presence probability distribution law fij, as a function of said statistical parameters, to identify the unknown material, said presence probability distribution depending on said calibration material.

2. The method according to claim 1, wherein L is between 100 and several thousands.

3. The method according to claim 1, wherein said presence probability distribution law is a density probability fij depending on the calibration material of material i and thickness j.

4. The method according to claim 1, wherein said statistical parameters include the variance of a coefficient α1 of vector αp for the L performances.

5. The method according to claim 1, further comprising determining attenuation or transmission coefficients or statistical parameters, as interpolated statistical parameters, for thickness values, as interpolation thicknesses, other than those determined during a).

6. The method according to claim 5, further comprising d') determining or calculating, for each calibration material and each of at least part of the interpolation thicknesses selected for each calibration material, a presence probability distribution law, as a function of said statistical parameters.

7. The method according to claim 1, said presence probability distribution being of Gaussian type.

8. The method according to claim 1, wherein, during b), at least L measurements are performed for each of the calibration materials and for each of the calibration thicknesses of selected calibration thicknesses, with $100 \leq L \leq 10^4$.

9. The method according to claim 1, wherein a flow of X-ray photons during b) is, for each measurement, at least equal to $10^6$ mm$^{-2}$s$^{-1}$.

10. A method for identifying the unknown material using X radiography, including measuring, for the unknown material, attenuation or transmission coefficients of X radiation, and determining at least a nature of the unknown material, by identifying the presence probability distribution law, among the distribution laws determined during a calibration method according to claim 1, having, for said attenuation or transmission coefficients, a maximum value.

11. The method according to claim 10, further comprising determining at least two transmission or attenuation coefficients ($\alpha_1$, $\alpha_2$), from said measured coefficients for the unknown material, in said at least two energy bands or ranges, one low energy, the other high energy, for each of the calibration materials and for each of the selected calibration thicknesses, the determination of at least the nature of the unknown material being performed by identifying the probability distribution which has, for these transmission or attenuation coefficients, the largest value.

12. The method according to claim 10, wherein the measurements of the attenuation or transmission coefficients are performed using a spectrometric sensor or one or more non-spectrometric sensors, or two sensors arranged in a sandwich.

13. The method according to claim 1, wherein the measurements of the attenuation or transmission coefficients are performed using a spectrometric sensor or one or more non-spectrometric sensors, or two sensors arranged in a sandwich.

14. A device for identifying X radiography materials, the device comprising:
circuitry configured to
a) determine at least one calibration material (i) and, for each material, at least one thickness (j) for the respective material,
b) measure, for each of the calibration materials and for each of the determined calibration thicknesses, N attenuation or transmission coefficients $\alpha_K$ for X radiation, with N≥2,
c) set up a vector $\vec{\alpha}_P$, said vector representing N attenuation or attenuation coefficients $\alpha_K$,
d) repeat operations b and c, with said calibration material, so that L vectors $\alpha_p$ are obtained, L representing the number of measurements performed with a same calibration material having material i and thickness j,
e) calculate statistical parameters from said L vectors $\alpha_p$;
f) determine or calculate, from said statistical parameters, a presence probability distribution law fij, as a function of said statistical parameters, said presence probability distribution depending on said calibration material, and
g) determine at least a nature of a material, as a function of said probability distribution laws, to identify the material.

15. The device according to claim 14, wherein the circuitry includes a spectrometric detector or one or more non-spectrometric sensors, or two sensors arranged in a sandwich to measure the attenuation or transmission coefficients.

16. The device according to claim 14, further comprising an X-ray source configured to emit a flow of incident photons at least equal to $10^6$ mm$^{-2}$s$^{-1}$.

17. The device according to claim 14, further comprising a detector of CdTe or CdMnTe, or HgI$_2$, or AsGa, or Si, or TlBr or CdZnTe type.

18. The device according to claim 14, wherein the circuitry is further configured to determine attenuation or transmission coefficients or statistical parameters, as attenuation or transmission coefficients or interpolated statistical parameters, for thickness values, as interpolation thicknesses, other than those for which one or more measurements are performed.

19. The device according to claim 18, wherein the circuitry is further configured to determine attenuation or transmission coefficients or statistical parameters from attenuation or transmission coefficients or interpolated statistical parameters and to calculate a presence probability distribution, as a function of said statistical parameters.

20. The device according to claim 14, wherein the circuitry is further configured to calculate at least two transmission or attenuation coefficients, in at least two energy bands or ranges, one being low energy and the other high energy, from the attenuation or transmission function measured for a material.

21. The device according to claim 20, wherein a first energy band or range is between 15 and 50 keV, and a second energy band or range is between 50 and 120 keV.

22. The device according to claim 20, wherein the statistical parameters include at least the average and standard deviation of each of the transmission or attenuation coefficients, and the coefficient of correlation between the calculated transmission or attenuation coefficients.

23. The device according to claim 20, wherein the circuitry is further configured to discretize the transmission or attenuation coefficients in N values.

* * * * *